(12) United States Patent
Rovati et al.

(10) Patent No.: US 11,590,114 B2
(45) Date of Patent: Feb. 28, 2023

(54) PHARMACEUTICAL COMBINATION OF AN EP4 ANTAGONIST AND IMMUNE CHECKPOINT INHIBITORS FOR THE TREATMENT OF TUMOURS

(71) Applicant: ROTTAPHARM BIOTECH S.R.L., Monza (IT)

(72) Inventors: Lucio Claudio Rovati, Monza (IT); Antonio Giordani, Pavia (IT); Filippo Magaraci, Monza (IT); Gianfranco Caselli, Milan (IT); Tiziana Piepoli, Milan (IT); Daniele Maggioni, Barzio (IT); Albino Bonazzi, Milan (IT)

(73) Assignee: ROTTAPHARM BIOTECH S.R.L., Monza (IT)

( * ) Notice: Subject to any disclaimer, the term of this patent is extended or adjusted under 35 U.S.C. 154(b) by 3 days.

(21) Appl. No.: 17/601,487

(22) PCT Filed: Apr. 8, 2020

(86) PCT No.: PCT/EP2020/060054
§ 371 (c)(1),
(2) Date: Oct. 5, 2021

(87) PCT Pub. No.: WO2020/208088
PCT Pub. Date: Oct. 12, 2020

(65) Prior Publication Data
US 2022/0142996 A1    May 12, 2022

(30) Foreign Application Priority Data
Apr. 9, 2019   (EP) .................................... 19168253

(51) Int. Cl.
| | | |
|---|---|---|
| *A61K 31/438* | (2006.01) |
| *A61P 35/00* | (2006.01) |
| *A61K 31/4458* | (2006.01) |
| *C07D 211/60* | (2006.01) |
| *C07D 221/20* | (2006.01) |
| *A61K 39/395* | (2006.01) |

(52) U.S. Cl.
CPC ........ *A61K 31/438* (2013.01); *A61K 31/4458* (2013.01); *A61K 39/3955* (2013.01); *A61P 35/00* (2018.01); *C07D 211/60* (2013.01); *C07D 221/20* (2013.01)

(58) Field of Classification Search
CPC .............. A61K 31/438; A61K 31/4458; C07D 211/60; C07D 221/20; A61P 35/00
See application file for complete search history.

(56) References Cited

FOREIGN PATENT DOCUMENTS

| WO | 2013004290 A1 | 1/2013 | |
| WO | WO-2013004290 A1 * | 1/2013 | ........... C07D 205/04 |
| WO | 2018008711 A1 | 1/2018 | |
| WO | 2018084230 A1 | 5/2018 | |
| WO | WO-2018084230 A1 * | 5/2018 | ........... A61K 31/192 |

OTHER PUBLICATIONS

Wikipedia. "CD276." Last modified Sep. 17, 2021. https://en.wikipedia.org/wiki/CD276. (Year: 2022).*
Wikipedia. "VTCN1." Last modified Sep. 23, 2021. https://en.wikipedia.org/wiki/VTCN1 (Year: 2022).*

* cited by examiner

*Primary Examiner* — Joseph R Kosack
*Assistant Examiner* — Sagar Patel
(74) *Attorney, Agent, or Firm* — Elmore Patent Law Group, P.C.; Carolyn Elmore; Joseph Zucchero

(57) ABSTRACT

The present invention provides a pharmaceutical combination comprising the EP4 antagonist of Formula (R)-4-(1-(6-(4-(trifluoromethyl)benzyl)-6-azaspiro[2.5]octane-5-carboxamido)cyclopropyl)-benzoic acid or a pharmaceutically acceptable salt thereof and at least one immune checkpoint inhibitor, preferably the sodium salt of (R)-4-(1-(6-(4-(trifluoromethyl)benzyl)-6-azaspiro[2.5]octane-5-carboxamido)cyclopropyl) benzoic acid. A polymorphic form A of sodium salt of (R)-4-(1-(6-(4-(trifluoromethyl) benzyl)-6-azaspiro[2.5]octane-5-carboxamido)cyclopropyl)benzoate characterized by a powder XRD spectrum with peaks at values of the angle $2\theta \pm 0.2°$ of 4.3, 5.0, 5.8, 6.4, 7.1, 8.3, 8.7, 12.8, 15.3, 15.9 is also described. The combination and the polymorphic form A are described for use in the treatment of tumours.

7 Claims, 9 Drawing Sheets

PHARMACEUTICAL COMBINATION OF AN EP4 ANTAGONIST AND IMMUNE CHECKPOINT INHIBITORS FOR THE TREATMENT OF TUMOURS

FIELD OF THE INVENTION

The present invention provides a pharmaceutical combination of an EP4 antagonist and immune checkpoint inhibitors to treat tumours.

In a preferred aspect, the invention concerns a polymorph of the EP4 antagonist of the combination of the invention.

BACKGROUND OF THE INVENTION

Cancer is a major threat to global public health and it is still a leading cause of death worldwide. Therefore, despite recent advances in therapy, there is an urgent medical need for the development of more effective therapeutic treatments.

Immuno-oncology is an innovative area of research that aims at harnessing the patient's immune system to fight cancer. One of the most promising approach to prevent suppression of anti-cancer immunity is the blockade of immune checkpoints, i.e. molecular pathways evolved to prevent T-cell-mediated autoimmunity, but that tumours can also exploit to their advantage. In tumours, the expression of these proteins is deregulated. For this reason, a significant line of research has focused on immune checkpoint inhibitors (ICI) to block the inhibitory receptors expressed on T cells, such as cytotoxic T-lymphocyte-associated protein-4 (CTLA-4) and programmed cell death protein-1 (PD-1) or their corresponding ligands expressed on tumour cells, such as programmed cell death ligand-1 (PD-L1). (Alsaab, H. O. et al. *Front. Pharmacol.* 8, 1-15 (2017)).

Different anti-cancer drugs focused on anti CTLA-4 and PD-1/PD-L1 checkpoint inhibitors are now approved by the FDA. These include monoclonal antibodies against PD-1 and CTLA-4, such as pembrolizumab, nivolumab, durvalumab, tremelimumab and ipilimumab. Cancer immunotherapy by blockade of immune checkpoint molecules has proved remarkable clinical efficacy across multiple cancer types, furthermore clinical trials of immune checkpoint immunotherapy have shown good results even for advanced metastatic cancers. (Alsaab, H. O. et al. *Front. Pharmacol.* 8, 1-15 (2017)).

Despite an unquestionable success, not all patients are responsive, probably because cancer can find other ways to escape immune surveillance. These limitations have pushed clinicians toward new antitumoral agents or new therapies that are more efficacious against immune surveillance

SUMMARY OF THE INVENTION

The inventors surprisingly found out that a combination of an EP4 antagonist and at least one immune checkpoint inhibitor is effective in the treatment of tumours.

Therefore the invention relates to a pharmaceutical combination comprising the EP4 antagonist of Formula (R)-4-(1-(6-(4-(trifluoromethyl)benzyl)-6-azaspiro[2.5]octane-5-carboxamido)cyclopropyl)benzoic acid or a pharmaceutically acceptable salt and at least one immune checkpoint inhibitor.

The EP4 antagonist was firstly described in WO2013/004290 as comprised in a general formula. The inventors surprisingly found out that the EP4 antagonist of Formula (R)-4-(1-(6-(4-(trifluoromethyl)benzyl)-6-azaspiro[2.5]octane-5-carboxamido) cyclopropyl) benzoic acid was the only one that, when combined with a check point inhibitor, was capable to efficaciously treat tumours as it will be evident from the experimental part.

When in the present invention the definition of "immune checkpoint" is used, it is intended as an accessory molecule capable to activate cellular pathways in immune cells or in cancer cells that either promote or inhibit T-cell activation.

When in the present invention the definition of "immune checkpoint inhibitor" is used, it is intended as a molecule that inhibits the function of an immune checkpoint.

The inventors surprisingly found out that the sodium salt of EP4 antagonist (R)-4-(1-(6-(4-(trifluoromethyl)benzyl)-6-azaspiro[2.5]octane-5-carboxamido)cyclopropyl) benzoic acid was the preferred one for preparing the combination. As it will be clear from the experimental part the sodium salt of (R)-4-(1-(6-(4-(trifluoromethyl)benzyl)-6-azaspiro[2.5]octane-5-carboxamido)cyclopropyl)benzoic acid as obtained was an amorphous compound. Surprisingly the inventors found out a very stable crystalline form of sodium (R)-4-(1-(6-(4-(trifluoromethyl)benzyl)-6-azaspiro[2.5]octane-5-carboxamido)cyclopropyl)benzoate named as Form A that allowed to treat cancers by itself, preferably when in combination with at least one immune checkpoint inhibitor.

Therefore in another aspect the invention concerns a polymorphic form A of sodium salt of (R)-4-(1-(6-(4-(trifluoromethyl)benzyl)-6-azaspiro[2.5]octane-5-carboxamido) cyclopropyl)benzoic acid characterized by a powder XRD spectrum with peaks at values of the angle $2\theta \pm 0.2°$ of 4.3, 5.0, 5.8, 6.4, 7.1, 8.3, 8.7, 12.8, 15.3, 15.9.

The invention further relates to the polymorphic form A of sodium salt of (R)-4-(1-(6-(4-(trifluoromethyl)benzyl)-6-azaspiro[2.5]octane-5-carboxamido)cyclopropyl) benzoic acid for use as a medicament, preferably for the use in the treatment of tumours.

The pharmaceutical combination hence preferably comprises the polymorphic form A of sodium salt of (R)-4-(1-(6-(4-(trifluoromethyl)benzyl)-6-azaspiro[2.5]octane-5-carboxamido)cyclopropyl)benzoic acid and at least one immune checkpoint inhibitor.

In another aspect, the invention relates to a pharmaceutical combination comprising the EP4 antagonist selected from (R)-4-(1-(6-(4-(trifluoromethyl)benzyl)-6-azaspiro [2.5]octane-5-carboxamido)cyclopropyl)benzoic acid or a pharmaceutically acceptable salt and at least one immune checkpoint inhibitor.

In another aspect, the invention relates to a pharmaceutical combination comprising the EP4 antagonist consisting of crystalline Form A of sodium (R)-4-(1-(6-(4-(trifluoromethyl)benzyl)-6-azaspiro[2.5]octane-5-carboxamido)cyclopropyl)benzoate and at least one immune checkpoint inhibitor for use in the treatment of tumours.

DETAILED DESCRIPTION OF THE INVENTION

Figure 1:
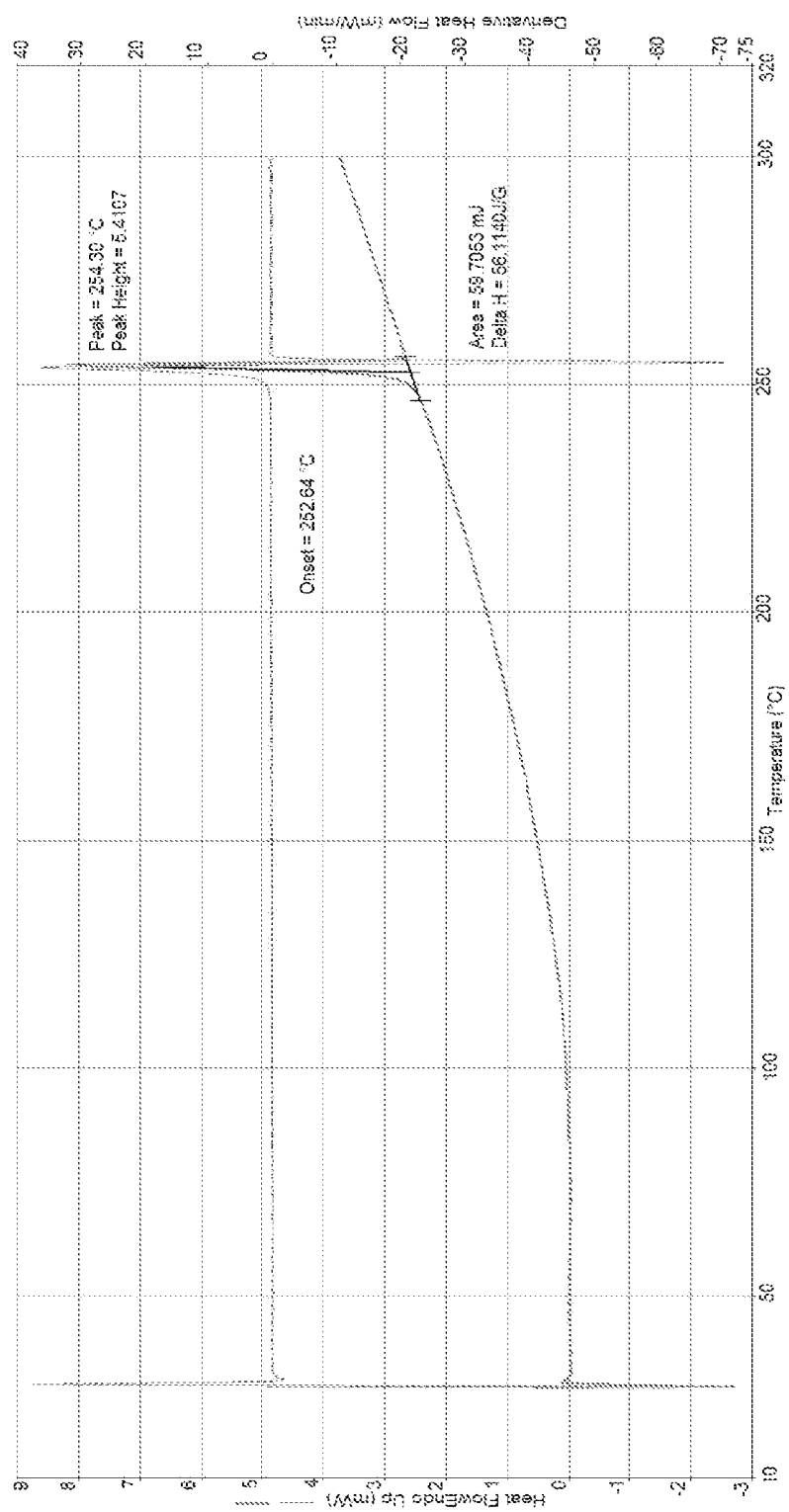
FIG. 1 reports the DSC graph of the crystalline form A of sodium (R)-4-(1-(6-(4-(trifluoromethyl)benzyl)-6-azaspiro [2.5]octane-5-carboxamido)cyclopropyl)benzoate of Example 1.

The invention relates to a pharmaceutical combination comprising the EP4 antagonist of Formula (R)-4-(1-(6-(4-(trifluoromethyl)benzyl)-6-azaspiro[2.5]octane-5-carboxamido)cyclopropyl)benzoic acid or a pharmaceutically acceptable salt thereof and at least one immune checkpoint inhibitor.

The combination of the invention can comprise a pharmaceutically acceptable salt of the EP4 antagonist (R)-4-(1-(6-(4-(trifluoromethyl)benzyl)-6-azaspiro[2.5]octane-5-carboxamido)cyclopropyl)benzoic acid. The salt can be selected from the group consisting of hydrochloride, sodium salt, potassium salt and lithium salt. Preferably according to the invention the salt of the combination is the sodium salt.

As it will be clear from the experimental part the sodium salt of (R)-4-(1-(6-(4-(trifluoromethyl)benzyl)-6-azaspiro [2.5]octane-5-carboxamido)cyclopropyl)benzoic acid as obtained was an amorphous compound.

Surprisingly the inventors found out a very stable crystalline form of sodium (R)-4-(1-(6-(4-(trifluoromethyl)benzyl)-6-azaspiro[2.5]octane-5-carboxamido)cyclopropyl) benzoate named as Form A to be used in combination with at least one immune checkpoint inhibitor.

Therefore in another aspect the invention concerns a polymorphic form A of sodium salt of (R)-4-(1-(6-(4-(trifluoromethyl)benzyl)-6-azaspiro[2.5]octane-5-carboxamido) cyclopropyl)benzoic acid characterized by a powder XRD spectrum with peaks at values of the angle 2θ±0.2° of 4.3, 5.0, 5.8, 6.4, 7.1, 8.3, 8.7, 12.8, 15.3, 15.9.

The invention further relates to the polymorphic form A of sodium salt of (R)-4-(1-(6-(4-(trifluoromethyl)benzyl)-6-azaspiro[2.5]octane-5-carboxamido)cyclopropyl) benzoic acid for use as a medicament, preferably for the use in the treatment of tumours.

The pharmaceutical combination hence preferably comprises the polymorphic form A of the sodium salt of (R)-4-(1-(6-(4-(trifluoromethyl)benzyl)-6-azaspiro[2.5]octane-5-carboxamido)cyclopropyl)benzoic acid and at least one immune checkpoint inhibitor. In another aspect the invention relates to a pharmaceutical combination comprising the EP4 antagonist selected from (R)-4-(1-(6-(4-(trifluoromethyl)benzyl)-6-azaspiro[2.5]octane-5-carboxamido)cyclopropyl)benzoic acid or a pharmaceutically acceptable salt and at least one immune checkpoint inhibitor for the use as a medicament.

In another aspect the invention relates to a pharmaceutical combination comprising the EP4 antagonist selected from (R)-4-(1-(6-(4-(trifluoromethyl)benzyl)-6-azaspiro[2.5]octane-5-carboxamido)cyclopropyl)benzoic acid or a pharmaceutically acceptable salt and at least one immune checkpoint inhibitor for the use in the treatment of tumours.

In another aspect, the invention relates to a pharmaceutical combination comprising the EP4 antagonist consisting of crystalline Form A of sodium (R)-4-(1-(6-(4-(trifluoromethyl)benzyl)-6-azaspiro[2.5]octane-5-carboxamido)cyclopropyl)benzoate and at least one immune checkpoint inhibitor for the use in the treatment of tumours.

Accordingly, the invention is further directed to a method of treating a tumour, which comprises administering to the patient a therapeutically effective amount of the pharmaceutical combination of the invention.

Immune checkpoint inhibitors comprise, but they are not limited to, PD-1 (Programmed Death-1), PD-L1 (Programmed Death-Ligand 1), CTLA-4 (Cytotoxic T lymphocyte Antigen-4), TIM3 (T cell immunoglobulin and mucin-3), OX-40 and its ligand OX40L, LAG-3 (lymphocyte activation gene-3), KIR (Killer-cell Immunoglobulin-like Receptor), VISTA (V-domain Ig-containing suppressor of T cell activation), IDO1 (Indoleamine 2,3-dioxygenase), TIGIT (T cell immunoglobulin and ITIM domain), BTLA (B and T lymphocyte attenuator), A2AR (Adenosine receptor A2), SIGLEC7 (Sialic acid-binding immunoglobulin-type lectin 7), GITR (Glucocorticoid-Induced TNFR family Related gene), ICOS (Inducible T-cell costimulator), NOX-2 (nicotinamide adenine dinucleotide phosphate NADPH oxidase isoform 2), Arginase I, CD276 (Cluster of Differentiation 276,also referred to as B7H4), CD27 (Cluster of Differentiation 27) and its ligand CD27 (Cluster of Differentiation 27), CD160 (Cluster of Differentiation 160) and CD39 (Cluster of Differentiation 39).

Preferably, immune checkpoint inhibitors are neutralizing antibodies anti PD-1 (e.g. Nivolumab (Opdivo), Pembrolizumab (Keytruda)), anti CTLA-4 (e.g., ipilimumab, Tremelimumab), anti TIM-3 antibodies (e.g. MBG453) or anti LAG-3 antibody.

The antibody, for example the anti PD-1 used in the present invention or antibody anti any of the other immune checkpoints as listed above, prior to administration will be generally mixed in a pharmaceutically acceptable substance, such as a physiological saline solution and it may be administered using any appropriate methods, including, but not limited to, intravenous, intradermal, intraperitoneal or intrathecal injection.

A therapeutically "effective amount" is intended to the amounts of the EP4 antagonist and of the at least one checkpoint inhibitor that will correspond to amounts that will vary depending upon factors such as the particular checkpoint inhibitor (e.g., the potency ($IC_{50}$), efficacy ($EC_{50}$), and the biological half-life of the particular checkpoint inhibitor), tumour condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compounds contained in the combination will vary according to the identity of the human in need of treatment (e.g., weight), the particular compound and its properties (e.g., pharmaceutical characteristics), tumour and its severity, that can nevertheless be determined by one of skill in the art.

The EP4 antagonist of the invention and the at least one immune checkpoint inhibitor of the invention may be administered, independently from each other, by any suitable route of administration, including both systemic administration and topical administration.

Systemic administration includes oral administration, parenteral administration, transdermal administration, rectal administration, and administration by inhalation.

The combination of EP4 antagonist of the invention and the at least one immune checkpoint inhibitor of the invention may be administered once or according to a dosing regimen wherein a number of doses are administered at varying intervals of time for a given period of time. Doses may be administered until the desired therapeutic effect is achieved or indefinitely to maintain the desired therapeutic effect. Suitable dosing regimens for the EP4 antagonist of the invention and the at least one immune checkpoint inhibitor of the invention depend on the pharmacokinetic properties of such compounds, such as absorption, distribution, and half-life, which can be determined by the skilled artisan. The combination of the invention can be also formulated into a pharmaceutical composition prior to administration to a patient. The pharmaceutical compositions of the invention are prepared using techniques and methods known to those skilled in the art.

In a more preferred aspect, the tumours may include, but they are not limited to colorectal cancers, bladder cancers, adrenal cancers, breast cancers, brain cancers, glioma, glioblastoma, cervical cancers, head and neck cancers, endometrial cancers, lung cancers, ovarian cancers, melanoma, prostate cancers, kidney cancers, renal cancers, liver cancers, thyroid cancers, pancreatic cancers, sarcoma, fibrosarcoma.

In an even more preferred aspect, the immune checkpoint inhibitors are anti CTLA-4 and/or anti PD-1/PD-L1 checkpoint inhibitors.

For all methods of treatment, in some embodiments, the effective dose of anti PD-1 antibody used is 0.1 mg/kg to 20 mg/kg of total body weight, with preferable doses of 2 mg/kg or 3 mg/kg.

It will also be recognized by one of skilled in the art that the optimal quantity and spacing of individual dosages will be determined by the nature and extent of the condition being treated.

The invention will be now further detailed with reference to the experimental part.

Experimental Part

Reagents used in the following examples were commercially available from various suppliers and used without further purifications. Solvents were used in dry form. Reactions in anhydrous environment were run under a positive pressure of dry $N_2$.

Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

Flash silica gel chromatography was performed on Biotage automatic flash chromatography systems (Isolera systems) using Biotage SNAP HP silica cartridges. Reverse phase chromatography was performed on Biotage automatic flash chromatography systems (Isolera systems) using RediSep Gold C-18Aq cartridges.

Purifications of some basic compounds were performed using Phenomenex Strata SCX cartridges (55 μm, 70 A).

Thin layer chromatography was carried out using Merck TLC plates Kieselgel 60E-254, visualized with UV light, aqueous permanganate solution, iodine vapours.

The following abbreviations are used herein: AcOH: acetic acid; DIAD: diisopropyl (E)-diazene-1,2-dicarboxylate; Boc: terbutyloxycarbonyl; DCM: dichloromethane; TFA: trifluoroacetic acid; DMF: dimethylformamide; THF: tetrahydrofuran; RT: room temperature; AcOEt: ethyl acetate; NaOH: sodium hydroxide; LiOH: lithium hydroxide; DIPEA: N,N-diisopropylethylamine; TEA: triethyl amine; $NaHCO_3$: sodium bicarbonate; $Na_2SO_4$: sodium sulphate; $Cs_2CO_3$: cesium carbonate; NaHMDS: Sodium bis(trimethylsilyl)amide; HOBt: 1-Hydroxybenzotriazole

EXAMPLE 1

Preparation of the EP4 antagonist of Formula (R)-4-(1-(6-(4-(trifluoromethyl)benzyl)-6-azaspiro[2.5]octane-5-carboxamido)cyclopropyl)benzoic acid, sodium salt The compound was obtained following the synthetic steps as in the following scheme

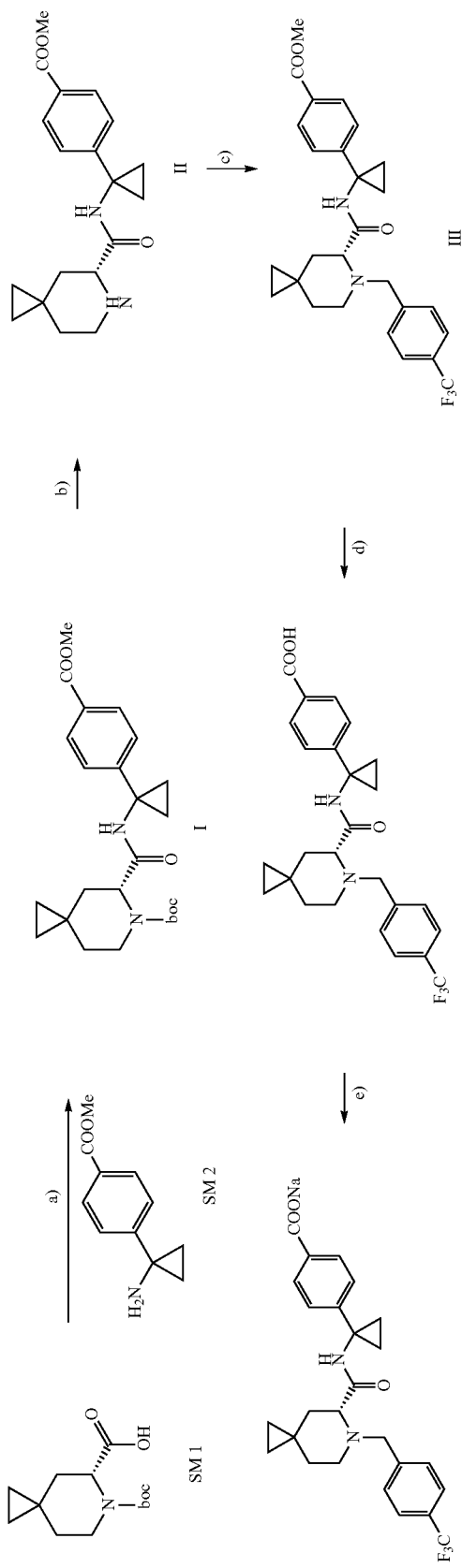

Compound 1 a) Conversion of the starting material (SM 1) into compound of formula (I), using starting material (SM 2) and a suitable coupling agent;
b) Deprotection of compound (I) in acidic media as TFA in DCM to obtain compound (II);
c) Alkylation of the nitrogen on the ring with a benzyl bromide in presence of a suitable inorganic base as NaOH to obtain compound (IV); and
d) Hydrolysis of the methyl ester using a suitable inorganic base as NaOH to obtain compound (IV); and
e) Formation and Crystallization of the sodium salt in a suitable solvent.

EXAMPLE 1a)

Synthesis of Starting Material 1 (SM 1)

The starting material SM1 reported in the above scheme 1 was obtained by the following steps reported in the scheme 2 below:

a) Conversion of (R)-1-(tert-butoxycarbonyl)-4-oxopiperidine-2-carboxylic acid
  (prepared according to Thetrahedron (1997) 15671-15680) into methyl ester (IX), using MeI and a suitable base as $Cs_2CO_3$
b) Wittig reaction using Methyl triphenyl phosphonium bromide in toluene to obtain compound (X)
c) Deprotection of the piperidine nitrogen using a suitable acidic reagent as HCl in MeOH and subsequent protection using Cbz chloride in DCM to obtain compound (XI)
d) Cyclopropane formation using an organometallic reagent as diethylzinc in THF, diiodomethane and TFA to obtain compound (XII)
e) Deprotection of the piperidine nitrogen using a reducing agent as hydrogen and palladium on charcoal in MeOH and subsequent protection using $(BOC)_2O$ to obtain compound (XIII)
f) Hydrolysis of the methyl ester using a suitable inorganic base as LiOH in THF/MeOH to obtain (SM 1)

Synthesis of Intermediate (IX) 1-(tert-butyl) 2-methyl (R)-4-oxopiperidine-1,2-dicarboxylate With reference to scheme 2 the intermediate (IX) was prepared.

In a round bottom flask, (R)-1-(tert-butoxycarbonyl)-4-oxopiperidine-2-carboxylic acid (10 g; 0.041 mol) was dissolved in DMF (25 ml) and cooled to 3° C. Cesium carbonate (0.6 eq.) was added, then methyl iodide (1.1 eq) was added dropwise: after 2 h at RT, the mixture was diluted with water (250 ml) and extracted with AcOEt (3×150 ml). Combined organic layers were washed with water (150 ml×3), followed by brine (150 ml), dried over sodium sulphate, filtered and concentrated at 40° C. to get the title compound (9 g; 85%) as a light brown solid.

1H NMR (400 MHz, CHLOROFORM-d) δ=5.28-4.75 (m, 1H), 4.13-4.03 (m, 1H), 3.76 (s, 3H), 3.72-3.55 (m, 1H), 2.92-2.70 (m, 2H), 2.53 (br s, 2H), 1.50 (br s, 9H) ESI+m/z 258 $[M+H]^+$

Synthesis of Intermediate (X) 1-(tert-butyl) 2-methyl (R)-4-methylenepiperidine-1,2-dicarboxylate With reference to scheme 2 the intermediate (X) was prepared.

Methyl triphenyl phosphonium bromide (1.1 eq) was dissolved in dry toluene (400 ml), cooled to 3° C. then a NaHMDS solution (1.05 eq) was slowly dropped. After 1 hour under nitrogen atmosphere at 3° C., intermediate (IX) (9 g, 0.035 mol) in dry toluene (200 ml) was added and stirred for 1 hour. After completion, the reaction was quenched with ice/water (800 ml), the two layers were separated, organic layer was washed with water (350 ml) followed by brine (350 ml), dried over sodium sulphate and concentrated. The residue was purified by column chromatography using silica gel eluting with Hexane/AcOEt 95-5 to 60-40 to afford the title compound as a pale yellow solid (8 g; 90%)

1H NMR (400 MHz, CHLOROFORM-d) δ=5.12-4.76 (m, 3H), 4.27-3.97 (m, 1H), 3.73 (s, 3H), 3.23-2.92 (m, 1H), 2.86-2.69 (m, 1H), 2.57-2.38 (m, 1H), 2.21 (br s, 2H), 1.49 (br s, 9H). ESI+m/z 256 $[M+H]^+$

Synthesis of Intermediate (XI) 1-benzyl 2-methyl (R)-4-methylenepiperidine-1,2-dicarboxylate With reference to scheme 2 the intermediate (XI) was prepared.

Intermediate (X) (8 g; 0.031 mol) was dissolved in dry methanol (150 ml), cooled to 0° C., then 300 ml 3M methanolic HCl solution were added slowly. After 2 hours at RT solvent was evaporated to dryness, residue dissolved in DCM (250 ml), cooled to 0° C., then triethylamine (2.5 eq) and benzylchloroformate (1.2 eq) were added after 1 hour at RT. After completion, the reaction was quenched with ice-cold water; the two layers were separated and the organic layer was washed with water followed by brine solution (250 ml). The organic layer was dried over sodium sulphate and concentrated below 40° C. to get a residue that was purified by column chromatography using silica gel eluting with Hexane/AcOEt 95-5 to 60-40 to afford the title compound as a white solid (6.7 g; 74%).

1H NMR (400 MHz, CHLOROFORM-d) δ=7.45-7.30 (m, 5H), 5.24-4.93 (m, 3H), 4.83 (s, 2H), 4.31-4.13 (m, 1H), 3.84-3.62 (m, 3H), 3.26-3.03 (m, 1H), 2.86-2.74 (m, 1H), 2.55-2.43 (m, 1H), 2.34-2.17 (m, 2H). ESI+m/z 290 $[M+H]^+$

Synthesis of intermediate (XII) 6-benzyl 5-methyl (R)-6-azaspiro [2.5] octane-5,6-dicarboxylate With reference to scheme 2 the intermediate (XII) was prepared.

DCM (150 ml) was cooled to 0° C., then diethyl zinc solution in THF (2.3 eq) was added slowly and stirred for 30 minutes. Trifluoro acetic acid (2.0 eq) was added slowly at 0° C. and stirred for 60 minutes, then diiodomethane (4.0 eq) was added and stirred for 60 minutes at 0° C. Intermediate (XI) (6 g; 0.02 mol) in dry dichloromethane (50 ml) was added slowly at 0° C., then left stirring at 25° C. for 20 hours. Reaction mass was quenched with 10% sodium bicarbonate solution (400 ml). The solid precipitate was filtered off, the layers were separated from the filtrate and the organic layer was washed with water (250 ml×2) followed by brine solution (250 ml). The organic layer was dried over sodium sulphate and concentrated below 40° C., obtaining a residue that was purified by column chromatography using silica gel eluting with Hexane/AcOEt 95-5 to 60-40 to afford the title compound as a white solid (4.72 g; 75%).

1H NMR (400 MHz, CHLOROFORM-d) d ppm 0.03-0.47 (m, 78H) 0.76-0.92 (m, 1H) 1.26-1.48 (m, 1H) 1.49-1.70 (m, 2H) 1.75 (s, 1H) 1.88-2.04(m, 1H) 2.19 (s, 1H) 2.35-2.41 (m, 1H) 3.17-3.39 (m, 1H) 3.61-3.83 (m, 3H) 4.14 (m, J=11.74 Hz, 1H) 4.96 (m, J=4.89 Hz, 1H) 5.12-5.25 (m, 2H)7.15-7.28 (m, 1H) 7.37 (m, J=9.29 Hz, 5H). ESI+m/z 304 [M+H]$^+$ Synthesis of intermediate (XIII) 6-(tert-butyl) 5-methyl (R)-6-azaspiro[2.5]octane-5,6-dicarboxylate With reference to scheme 2 the intermediate (XIII) was prepared.

Intermediate (XII) (4.5 g, 0.015 mol) was dissolved in methanol (200 ml), Pd/C 10% (400 mg) was added, then the suspension was hydrogenated at 3 bars for 2 hours. After completion, the reaction was filtered through celite bed, washing with methanol (200 ml). The solution was concentrated to 150 ml, cooled to 20° C. then slowly added boc-anhydride (1.2 eq) and stirred for 16 hrs at 25 5° C. After reaction completion, the solvent was evaporated, then the residue purified by column chromatography using silica gel eluting with Hexane/AcOEt 95-5 to 60-40 to afford the title compound as a white solid (3.68 g; 92%).

1H NMR (400 MHz, CHLOROFORM-d) δ=5.03-4.71 (m, 1H), 4.21-3.90 (m, 1H), 3.74 (s, 3H), 3.35-3.04 (m, 1H), 2.27-2.13 (m, 1H), 2.02-1.83 (m, J=4.6, 13.1, 13.1 Hz, 1H), 1.56-1.38 (m, 10H), 0.95-0.72 (m, 1H), 0.43-0.20 (m, 4H). ESI+m/z 270 [M+H]$^+$

Synthesis of Starting Material 1 (SM 1) (R)-6-(tert-butoxycarbonyl)-6 azaspiro[2.5]octane-5-carboxylic acid With reference to scheme 2 the starting material (SM1) was obtained.

Intermediate (XIII) (3.5 g; 0.013 mol) was dissolved in THF (100 ml) and methanol (100 ml), cooled to 0° C., then lithium hydroxide solution (3.0 eq in 50 ml of water) was dropped.

The mixture was stirred at RT for 8 hours. The reaction was cooled to 10° C., quenched with acetic acid to pH 5 (50 ml), concentrated by distilling off MeOH and THF. The concentrated mass was diluted with ice-water and extracted with ethyl acetate (300 ml×2). Combined organic layers were washed with water (200 ml) followed by brine (200 ml). The organic layer was dried over sodium sulphate and concentrated below 50° C. To the residue petroleum ether (300 ml) was added; the solid was filtered off and vacuum dried for 24 hours at 40° C. Yield 3 g (92%)

1H NMR (400 MHz, CHLOROFORM-d) δ=5.11-4.77 (m, 1H), 4.18-3.88 (m, 1H), 3.32-3.09 (m, 1H), 2.32-2.14 (m, 1H), 2.03-1.88 (m, 1H), 1.67-1.55 (m, 1H), 1.50 (br s, 9H), 0.97-0.75 (m, 1H), 0.52-0.26 (m, 4H). ESI+m/z 256 [M+H]$^+$

EXAMPLE 1b

Synthesis of Starting Material 2 (SM 2)

The starting material 2 (SM 2) was prepared according to known literature procedures (WO2008104055, example 1, step 2).

EXAMPLE 1c

Synthesis of Intermediate (I) tert-butyl (R)-5-((1-(4-(methoxycarbonyl) phenyl)cyclopropyl)carbamoyl)-6-azaspiro[2.5]octane-6-carboxylate With reference to scheme 1 the intermediate (I) was obtained.

10 g (0.039 mmol) of starting material 1 were dissolved in DCM (200 ml), HOBt hydrate (1.1 eq) and EDC-HCl (1.1 eq) were added and the mixture was stirred at 20° C. for 30 minutes. Starting material 2 (1.02 eq) was added, then TEA (1.2 eq.); the reaction was left stirring for 6 hours at 30° C., then was quenched with water (100 ml). The organic phase was washed with 5% sodium bicarbonate solution (100 ml),1M citric acid solution (200 ml), water (200 ml). DCM was evaporated, t-butylmethyl ether (200 ml) was added then the solvent was evaporated again. 400 ml of t-butylmethyl ether was added, the suspension was stirred at 20° C. for 17 hours, then the white solid was filtrated and washed with cool t-butylmethyl ether. The product was dried under vacuum at 50° C.

Yield 14.7 g (88%)

1H NMR (400 MHz, CHLOROFORM-d) δ=8.01-7.93 (m, 2H), 7.28 (s, 2H), 6.74 (s, 1H), 4.83 (br s, 1H), 4.21 (br s, 1H), 3.92 (s, 3H), 3.10-2.87 (m, 1H), 2.10-1.99 (m, 1H), 1.97-1.85 (m, 1H), 1.84-1.75 (m, 1H), 1.52 (s, 9H), 1.40 (br s, 4H), 0.88-0.81 (m, 1H), 0.63-0.45 (m, 1H), 0.45-0.29 (m, 2H), 0.28-0.18 (m, 1H). ESI+m/z 429 [M+H]$^+$

EXAMPLE 1d

Synthesis of Intermediate (II) methyl (R)-4-(1-(6-azaspiro[2.5]octane-5-carboxamido)cyclopropyl) benzoate With reference to scheme 1 the intermediate (II) was obtained.

Intermediate (I) (14 g; 0.032 mmol) was dissolved in DCM (150 ml), TFA (10 eq.) was added and the solution stirred at 20° C. for 5 hours. Reaction mixture was distilled under vacuum, DCM (100 ml) was added, saturated sodium bicarbonate solution was slowly added at 15-25° C. (300 ml, significant foaming). Organic phase was washed with water (200 ml) and evaporated at reduced pressure. t-butylmethyl ether (200 ml) was added then the solvent was evaporated again. 300 ml of t-butylmethyl ether was added, the suspension was stirred at 20° C. for 17 hours, then the white solid was filtrated and washed with cool t-butylmethyl ether. The product was dried under vacuum at 50° C.

Yield 9.65 g (90%)

1H NMR (400 MHz, CHLOROFORM-d) δ=7.96 (d, J=8.3 Hz, 2H), 7.61 (br s, 1H), 7.26 (d, J=8.3 Hz, 2H), 3.91

(s, 3H), 3.46-3.39 (m, 1H), 3.13-3.04 (m, 1H), 2.92-2.82 (m, 1H), 1.87-1.70 (m, 3H), 1.41-1.28 (m, 5H), 1.01-0.93 (m, 1H), 0.46-0.24 (m, 4H). ESI+m/z 329 [M+H]$^+$

EXAMPLE 1e

Synthesis of Intermediate (III) methyl (R)-4-(1-(6-(4-(trifluoromethyl) benzyl)-6-azaspiro[2.5]octane-5-carboxamido)cyclopropyl)benzoate With reference to scheme 1 the intermediate (III) was obtained.

Intermediate (II) (9.5 g, 0.029 mmol) was dissolved in dry THF (150 ml), then Cs$_2$CO$_3$ (2 eq) and 4-(trifluoromethyl) benzyl bromide (1.2 eq dissolved in 75 ml of THF) were added. Reaction mixture was stirred at 25° C. for 8 hours, then 350 ml of DCM and 350 ml of water were added. Organic phase was washed with water (150 ml) and brine (250 ml) and evaporated at reduced pressure. n-heptane (1500 ml) was added then the solvent was evaporated again. 150 ml of n-heptane was added, the suspension was stirred at 20° C. for 4 hours, then the white solid was filtrated and washed with n-heptane. The product was dried under vacuum at 50° C. Yield 12.95 g (92%)

1H NMR (400 MHz, CHLOROFORM-d) δ=7.96-7.89 (m, 2H), 7.66-7.61 (m, 2H), 7.47-7.40 (m, 3H), 7.27-7.21 (m, J=8.8 Hz, 2H), 3.90 (s, 3H), 3.84 (d, J=14.7 Hz, 1H), 3.35 (d, J=14.7 Hz, 1H), 3.05 (dd, J=3.9, 10.3 Hz, 1H), 2.93-2.86 (m, 1H), 2.31-2.22 (m, 1H), 2.07-1.98 (m, 1H), 1.88-1.78 (m, 1H), 1.45-1.27 (m, 4H), 1.17-1.08 (m, 1H), 1.01-0.94 (m, 1H), 0.50-0.36 (m, 3H), 0.33-0.26 (m, 1H). ESI+m/z 487 [M+H]$^+$

EXAMPLE 1f

Synthesis of Intermediate (IV) (R)-4-(1-(6-(4-(trifluoromethyl)benzyl)-6-azaspiro[2.5]octane-5-carboxamido)cyclopropyl)benzoic acid With reference to scheme 1 the intermediate (IV), the EP4 antagonist in the form of acid was obtained.

Intermediate (III) (12 g, 0.024 mmol) was dissolved in THF (70 ml), then NaOH 2N (4 eq) was added. The reaction was left stirring at 5° C. for 5 hours, then water (200 ml) was added and organics evaporated. 200 ml of dichloromethane was added and pH of the mixture was adjusted to 4.5-5.0 with acetic acid; the organic phase was washed with water and brine (200 ml×3), evaporated to obtain the title compound (9.9 g; 85%)

$^1$H NMR (400 MHz, DMSO-d6) δ ppm 12.72 (1H, s), 8.73 (1H, s), 7.78 (2H, d, J=8.6 Hz), 7.69 (2H, d, J=8.3 Hz), 7.64 (2H, d, J=8.3 Hz), 7.20 (2H, d, J=8.6 Hz), 3.79 (2H, d, J=13.9 Hz), 3.28 (1H, d, J=13.9 Hz), 2.93 (1H, dd, J=3.1; 10.3 Hz), 2.73 (1H, m), 2.08(2H, m), 1.78 (1H, m), 1.10-1.31 (5H, m), 0.87 (1H, m), 0.32 (4H, m). ESI+m/z 473 [M+H]$^+$.

The EP4 antagonist thus obtained was analyzed and it was found out that it was a zwitterion as an amorphous solid.

EXAMPLE 1g

Preparation of Sodium Salt of R)-4-(1-(6-(4-(trifluoromethyl)benzyl)-6-azaspiro[2.5]octane-5-carboxamido)cyclopropyl)benzoic acid The only crystalline forms which could be obtained from the zwitterion of Example 1f) were solvates, which easily gave rise to the amorphous form on thermal (e.g. heating to reduce solvent content to ICH level) or mechanical stress.

It was hence prepared a hydrochloride salt by adding to the intermediate (IV) HCl in ethyl ether.

The hydrochloride of intermediate (IV) was investigated and an amorphous form and two crystalline forms (anhydrous A and solvate B) were identified from the screening.

The anhydrous form A was further investigated. Intermediate (IV) hydrochloride form A showed tendency to convert to amorphous form under mechanical or thermal stress. Chemical stability was comparable with that of the amorphous zwitterion of example 1f).

A sodium salt was prepared by adding NaOH in EtOH after solubilization of intermediate (IV) in a solvent. Different solvents were tested (n-propanol, n-butanol; iPrOH), but n-propanol was selected for higher yields and easy drying. Two crystalline forms were obtained that were called forms A and D: form A was obtained directly from n-propanol crystallization, form D was obtained only by hydration of form A. During physical stability testing form D was found prone to conversion to the amorphous form by mechanical stress (milling) and during drying.

Conversely, sodium salt form A was found more stable towards amorphization by thermal stress, although amorphization was observed by mechanical stress at high energy. Form A was the most thermodynamically stable anhydrous form, Form D was the most stable hydrated form. Other forms were either less stable or metastable. These forms, as well as amorphous form, were easily converted to the stable form A by solid slurry from acetone, diethyl ether, isopropyl acetate, THF, heptane.

A synthesis protocol for sodium (R)-4-(1-(6-(4-(trifluoromethyl) benzyl)-6-azaspiro[2.5]octane-5-carboxamido) cyclopropyl)benzoate (Form A) (named also as Compound 1) was established as reported in the following.

Intermediate (IV) (50 g, 0.1 mol) was dissolved in n-propanol (400 ml), then a cooled solution of NaOH (1.02 eq) in EtOH (70 ml) was added. The suspension was stirred at 20-24° C. for 18-20 hours, then filtered, washed with pre-cooled n-propanol (100 ml) and dried at 70° C. for 24 hours. Yield 43 g white solid (87%)

$^1$H NMR (400 MHz, DMSO-d6) δ ppm 8.68 (1H, s), 7.73 (2H, d, J=8.3 Hz), 7.69 (2H, d, J=8.3 Hz), 7.64 (2H, d, J=8.3 Hz), 7.02 (2H, d, J=8.3 Hz), 3.81 (2H, d, J=13.9 Hz), 3.26 (1H, d, J=13.9 Hz), 2.92 (1H, dd, J=3.1; 10.5 Hz), 2.72 (1H, m), 2.07 (2H, m), 1.78 (1H, m), 1.16 (4H, m), 1.09 (1H, m), 0.85 (1H, m), 0.30 (4H, m). ESI+m/z 473 [M+H]$^+$ Solubility, dissolution and bioavailability studies were performed on both the zwitterion of example 1f), salt forms and all sodium forms. Salts (especially both forms of the sodium salt) showed improved dissolution properties in comparison to the amorphous. PK experiments in both rat and dog showed no significant difference between the various forms in terms of exposure and bioavailability, but the sodium salt form A appears to be the form of choice for development in view of the stability and pharmaceutical manufacturability properties.

Characterization of sodium (R)-4-(1-(6-(4-(trifluoromethyl) benzyl)-6-azaspiro [2.5] octane-5-carboxamido)cyclopropyl)benzoate (Form A) (named also as Compound 1)
Solid State NMR Solid-state NMR measurements were run on a Bruker AVANCE II 400 instrument operating at 400.23 and 100.65 MHz for 1H and 13C, respectively. $^{13}$C CPMAS spectra were recorded at room temperature at the spinning speed of 12 kHz. Cylindrical 4 mm o.d. zirconia rotors with sample volume of 80 μL were employed. For CPMAS experiments, a ramp cross polarization pulse sequence was used with a contact time of 3 ms, a 1H 90° pulse of 4.0 µs, recycle delays of 5-10 s, and 2000-4000 transients. The two pulse phase modulation decoupling scheme was used with a frequency field of 75 KHz $^{13}$C chemical shifts (ppm)

δ=177.1; 144.8; 143.1; 136.9; 129.3; 124.9; 71.4; 65.5; 61.3; 57.3; 51.2; 39.0; 35.1; 23.2; 18.0; 14.9; 12.6

XRPD

XRPD measurements were run on X-ray powder diffractometer PANalytical X'pert Pro with Bragg-Brentano geometry and equipped with:

a) Detector X'Celerator
b) Multisampler
c) Spinner
d) Ceramic X-ray tube Cu LFF ($\lambda_1$=1.54051 A; $\lambda_2$=1.54430 A)

Range 4-40° 2θ

| Characteristic peaks (°2θ) |
| --- |
| 4.3 ± 0.2°2θ |
| 5.0 ± 0.2°2θ |
| 5.8 ± 0.2°2θ |
| 6.4 ± 0.2°2θ |
| 7.1 ± 0.2°2θ |
| 8.3 ± 0.2°2θ |
| 8.7 ± 0.2°2θ |
| 12.8 ± 0.2°2θ |
| 15.3 ± 0.2°2θ |
| 15.9 ± 0.2°2θ |

DSC

The thermogram was acquired using a Perkin-Elmer DSC8000, the scan rate was 10° C./min from 30° C. to 300° C. The thermogram is reported in FIG. 1 Detected peak: T onset=252.64° C., ΔH=56.11 J/g

IR

Figure 2:
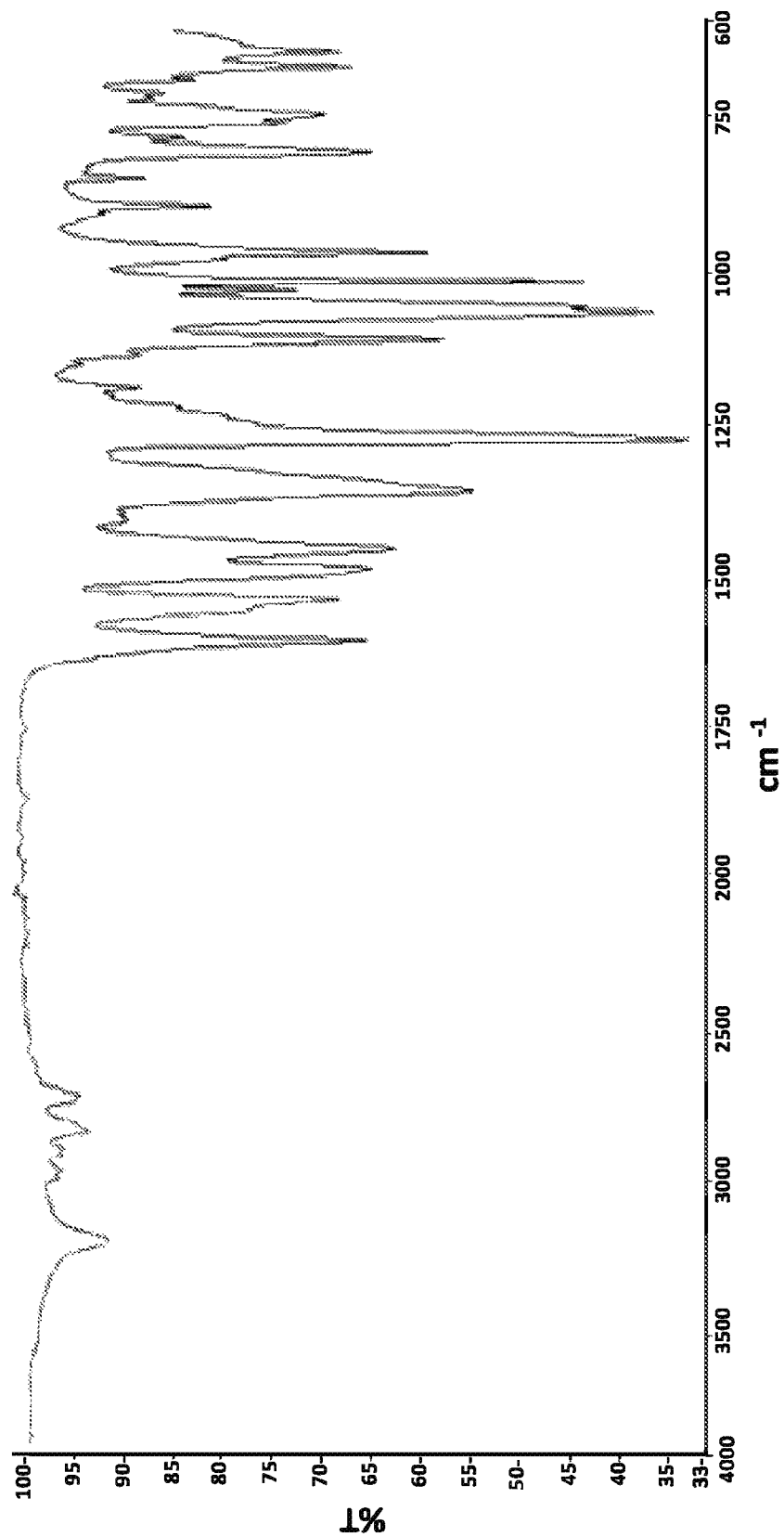
FIG. 2 reports the IR spectrum of the crystalline form A of sodium (R)-4-(1-(6-(4-(trifluoromethyl)benzyl)-6-azaspiro[2.5]octane-5-carboxamido)cyclopropyl)benzoate of Example 1.

The IR spectrum was recorded on a Perkin Elmer Spectrum 100 FT/IR instrument between 4000 and 650 cm$^{-1}$ by means of the ATR (Attenuated Total Reflectance) mode. The IR spectrum is reported in FIG. 2. The main absorption frequencies are reported in the following table:

| Band (cm$^{-1}$) |
| --- |
| 3301 |
| 2996 |
| 2938-2821 |
| 1659 |
| 1590 |
| 1540 |
| 1411 |

Stability of Form A

The stability of the Form A (named also as Compound 1) of the sodium salt of (R)-4-(1-(6-(4-(trifluoromethyl)benzyl)-6-azaspiro[2.5]octane-5-carboxamido)cyclopropyl)benzoic acid at different humidity values and temperatures was investigated. The results are reported in the following table:

| | RT | 50% RH-30° C. | 70% RH-40° C. | 90% RH-30° C. | 80° C. |
| --- | --- | --- | --- | --- | --- |
| Powder | Stable > 1 month | Stable > 24 hours | Stable up to 4 hours | Stable up to 4 hours | Stable > 5 days |
| Sealed foil/Poly bag | | | Stable > 3 months | | |

RH = relative humidity

EXAMPLE 2

Preparation of (R)-4-(1-(1-(4-(trifluoromethyl) benzyl) piperidine-2-carboxamido) cyclopropyl)benzoic acid, sodium salt (named also as Compound 2)

The EP4 antagonist of example 1 was compared with another EP4 antagonist disclosed in WO2013/004290, i.e. (R)-4-(1-(1-(4-(trifluoromethyl) benzyl) piperidine-2-carboxamido)cyclopropyl)benzoic acid.

The compound was obtained following the synthetic steps as in the following scheme 3:

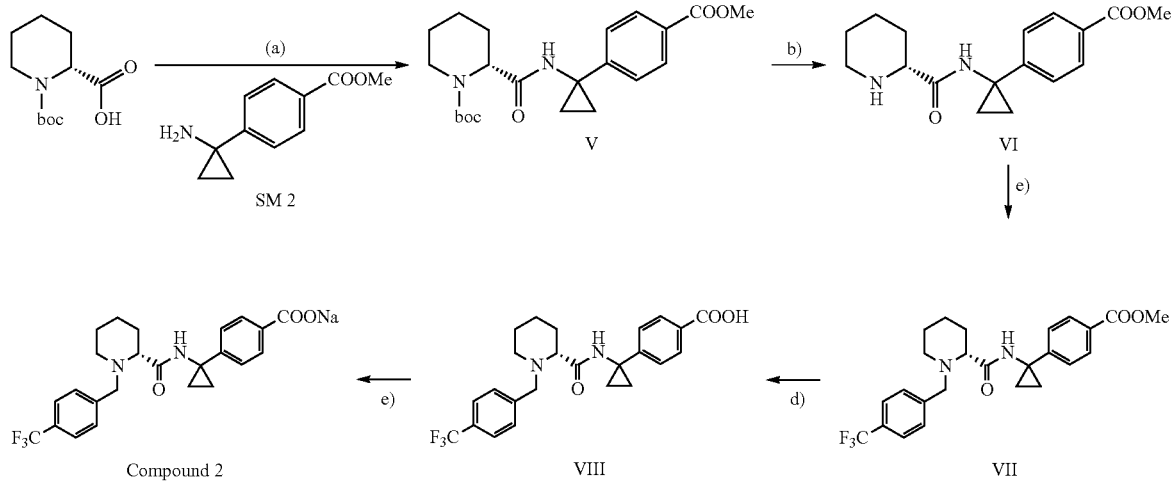

a) Conversion of (R)-1-(tert-butoxycarbonyl)piperidine-2-carboxylic acid into compound of formula (V), using starting material (SM2) and a suitable coupling agent;
b) Deprotection of compound (V) in acidic media as TFA in DCM to obtain compound (VI);
c) Alkylation of the nitrogen on the ring with a benzyl bromide in presence of a suitable base to option compound (VII);
d) Hydrolysis of the methyl ester using a suitable inorganic base as LiOH to obtain compound (VIII); and
e) Formation of the sodium salt using NaOH in suitable solvent mixture

EXAMPLE 2a

Synthesis of Intermediate (V) tert-butyl (R)-2-((1-(4-(methoxycarbonyl) phenyl)cyclopropyl)carbamoyl)piperidine-1-carboxylate Boc-D-pipecolic acid (500 mg, 2.181 mmol) was dissolved in DCM (13 ml). N-hydroxybenzotriazole hydrate (2.62 mmol) and EDCI (3.05 mmol) were added and the reaction mixture was left stirring for 40 min. SM2 (2.268 mmol) was added followed by TEA (2.94 mmol). The reaction mixture was left stirring at room temperature for 15 h, then water (20 ml) was added. Phases were separated and the aqueous layer was extracted with DCM (2×15 mL). The combined organic layers were evaporated and loaded on SNAP Ultra-HP Sphere-Si (10 g) column eluting with cyclohexane/AcOEt 100% up to 70/30. Yield 810 mg (92%), light yellow foam.

$^1$H NMR (400 MHz, CHLOROFORM-d) δ=8.00-7.93 (m, J=8.3 Hz, 2H), 7.27-7.22 (m, J=8.3 Hz, 2H), 6.76 (br s, 1H), 4.85-4.67 (m, 1H), 4.12 (br s, 1H), 3.92 (s, 3H), 2.97-2.66 (m, 1H), 2.29 (br s, 1H), 1.72-1.59 (m, 3H), 1.54-1.22 (m, 15H). ESI+m/z 403 [M+H]$^+$

EXAMPLE 2b

Synthesis of Intermediate (VI) methyl (R)-4-(1-(piperidine-2-carboxamido)cyclopropyl)benzoate Following the scheme 3, the intermediate (VI) was obtained.

Intermediate (V) (800 mg, 1.988 mmol) was dissolved in DCM (8 mL). TFA (19.88 mmol) was added and the reaction mixture was left stirring at room temperature for 4 hours. Solvents were evaporated and the residue was loaded on SPE-SCX (5 g) cartridges eluting with MeOH and NH$_3$ 1M in MeOH. Ammonia fractions were evaporated to obtain the title compound (590 mg; 98%)

1H NMR (400 MHz, CHLOROFORM-d) δ=8.00-7.92 (m, J=8.8 Hz, 2H), 7.58 (br s, 1H), 7.28-7.24 (m, 2H), 3.91 (s, 3H), 3.33-3.27 (m, 1H), 3.10-3.03 (m, 1H), 2.80-2.69 (m, 1H), 2.20 (br s, 1H), 2.06-1.97 (m, 1H), 1.84-1.74 (m, 1H), 1.65-1.58 (m, 1H), 1.54-1.31 (m, 7H). ESI+m/z 303 [M+H]$^+$

EXAMPLE 2c

Synthesis of Intermediate (VII) methyl (R)-4-(1-(1-(4-(trifluoromethyl) benzyl)piperidine-2-carboxamido)cyclopropyl)benzoate Intermediate (VI) (585 mg, 1.9 mmol) was dissolved in THF (12 ml). The mixture was stirred until the material was dissolved. Cesium carbonate (3.87 mmol) followed by 4-(Trifluoromethyl)benzyl bromide (2.42 mmol) was added and the mixture was stirred for 24 h. THF was evaporated and the residue taken up into a mixture of DCM/NaHCO$_3$ sat. sol (50 ml). Phases were separated and the aqueous layer was extracted with DCM (2×15 ml). The combined organic layers were evaporated and the residue was loaded on SNAP Ultra-HP Sphere-Si (10 g) column eluting with cyclohexane/ethyl acetate 100% up to 70/30. Yield 850 mg (95%)

1H NMR (400 MHz, DMSO-d6) δ=8.71 (s, 1H), 7.84-7.78 (m, 2H), 7.72-7.66 (m, 2H), 7.63-7.58 (m, 2H), 7.26-7.20 (m, J=8.8 Hz, 2H), 3.82 (s, 3H), 3.73 (d, J=14.2 Hz, 1H), 3.25 (d, J=14.2 Hz, 1H), 2.87-2.80 (m, 1H), 2.79-2.70 (m, J=11.7 Hz, 1H), 2.01-1.93 (m, 1H), 1.86-1.78 (m, 1H), 1.70 (br d, J=10.3 Hz, 2H), 1.57-1.38 (m, 2H), 1.35-1.23 (m, 3H), 1.21-1.11 (m, 2H). ESI+m/z 461 [M+H]$^+$

EXAMPLE 2d

Synthesis of Intermediate (VIII) (R)-4-(1-(1-(4-(trifluoromethyl) benzyl)piperidine-2-carboxamido) cyclopropyl)benzoic acid Lithium hydroxide monohydrate (3.32 mmol) was added to a solution of intermediate (VII) (850 mg, 1.846 mmol) in water/dioxane. The reaction mixture was left stirring at room temperature for 5 h, then 1 ml of AcOH was added, dioxane was evaporated and the residue was loaded on a Biotage C18 10 g SPE-column, eluting with water (2VC) and MeOH (3VC). Yield 94% (772 mg, white solid)

1H NMR (400 MHz, DMSO-d6) δ=12.72 (br s, 1H), 8.69 (s, 1H), 7.83-7.76 (m, 2H), 7.72-7.66 (m, 2H), 7.64-7.59 (m, 2H), 7.24-7.18 (m, 2H), 3.74 (d, J=14.2 Hz, 1H), 3.25 (d, J=14.2 Hz, 1H), 2.88-2.79 (m, 1H), 2.79-2.72 (m, 1H), 2.01-1.93 (m, 1H), 1.88-1.77 (m, 1H), 1.76-1.63 (m, 2H), 1.57-1.38 (m, 2H), 1.37-1.21 (m, 3H), 1.21-1.09 (m, 2H). ESI+m/z 447 [M+H]$^+$

EXAMPLE 2e

Synthesis of (R)-4-(1-(1-(4-(trifluoromethyl) benzyl) piperidine-2-carboxamido)cyclopropyl)benzoic acid, Sodium salt Intermediate (VIII) (40 g, 89.7 mmol) was dissolved in water/dioxane, then NaOH (98 mmol) was added. After stirring for 1 hour, THF was evaporated. The residue was loaded on was loaded on a Biotage C18 150 g SPE-column (8 injections), eluting with water (4VC) to MeOH (gradient 4CV). The fractions containing the desired product were evaporated and the obtained solid was dried under vacuum at 60° C. for 3 days. Yield 98% (41 g, white solid).

1H NMR (400 MHz, DMSO-d6) δ=8.60 (s, 1H), 7.75-7.65 (m, J=7.8, 7.8 Hz, 4H), 7.65-7.57 (m, 2H), 7.05-6.96 (m, 2H), 3.75 (d, J=14.2 Hz, 1H), 3.24 (d, J=13.7 Hz, 1H), 2.84-2.78 (m, 1H), 2.78-2.71 (m, J=11.7 Hz, 1H), 2.01-1.91 (m, 1H), 1.86-1.76 (m, 1H), 1.74-1.63 (m, 2H), 1.56-1.36 (m, 2H), 1.34-1.20 (m, 1H), 1.19-1.00 (m, 4H). ESI+m/z 447 [M+H]$^+$

EXAMPLE 3

Effect of combination therapy of Compound 1 (Form A of the sodium salt of (R)-4-(1-(6-(4-(trifluoromethyl)benzyl)-6-azaspiro[2.5]octane-5-carboxamido)cyclopropyl) benzoic acid) and Compound 2 with anti mouse pd-1 antibody in a syngeneic model of mouse colorectal cancer.

Material and Methods

Male Balb/c mice 4-6 weeks old were housed five per cage in a temperature and humidity controlled room with a 12 h/12 h light/dark cycle. Throughout the experiment the animals had free access to food and water. The Balb/c mice were randomly divided into 6 groups (n=15 in each group): vehicle, Compound 1, Compound 2, anti PD-1, Compound 1+anti PD-1, Compound 2+anti PD-1 group.

CT26 cells were purchased from ATCC and cultured in Dulbecco's Modified Eagle's Medium (DMEM; ThermoFisher Scientific) supplemented with 10% fetal bovine serum (FBS; Sigma Aldrich) at 37° C. in an incubator with 5% CO$_2$. Cells were sub-cultured twice a week until the number of cells needed for inoculation was obtained.

On the day of transplantation (day 0) logarithmic growing phase cells were harvested, diluted in PBS and $10^{\wedge}6$ cells in 0.2 ml of PBS were subcutaneously inoculated into the lateral abdominal region of each mouse using a 26G syringe.

On day 7 after inoculation the mice were randomized into the 6 treatment groups each of 15 animals receiving respectively vehicle, Compound 1, Compound 2, anti PD-1 and the combination therapies.

Compound 1 and the compound 2 were repeatedly administered orally from day 7 to day 23, 30 mg/kg once a day, while the anti mouse PD-1 antibody was intraperitoneally administered to the mice of the anti-mouse PD-1 antibody-single therapy group and to mice of the combination therapy group at a dose of 20 mg/kg on day 8 after the transplantation and at a dose of 10 mg/kg on day 13, on day 19 and on day 22 after the transplantation.

Tumour sizes ($mm^3$) were evaluated twice a week by using a digital caliper. The tumour volumes were calculated measuring the tumour lengths along the major and minor axis and using the formula: Volume=$[(Length)^2 \times Width]/2$.

Results

To investigate the effect of the combination therapy with Compound 1 and compound of example 2 and an anti-mouse PD-1 antibody an allograft model of a mouse colorectal cancer cell line was used. CT26 cancer cell tumours that were grown subcutaneously in mice were treated with Compounds of examples 1 or 2 single therapy or with compounds of examples 1 or 2 in combination therapy with an anti mouse PD-1 antibody for a period of 3 weeks.

Figure 3:
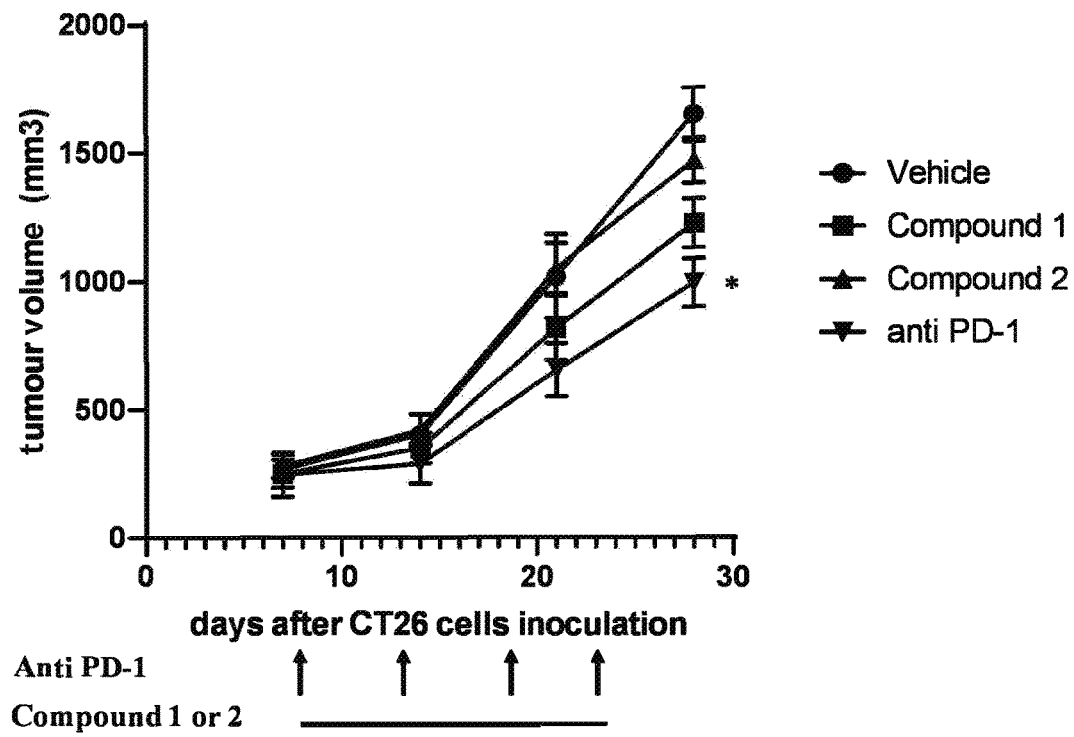
FIG. 3 reports the antitumor responses of the crystalline form A of sodium (R)-4-(1-(6-(4-(trifluoromethyl)benzyl)-6-azaspiro[2.5]octane-5-carboxamido)cyclopropyl) benzoate of Example 1, and of the comparison compound of example 2 and anti-PD-1 in CT26 Tumour Models. Balb/c mice were subcutaneously injected with 1×10^6 CT26 cells. After tumours were measured on day 7, mice were randomized and then treated with the designated therapy. The Compound 1 and the compound of example 2 were orally administered 30 mg/Kg daily. Anti PD-1 antibodies were injected 20 mg/kg on day 8 and 10 mg/kg on day 13, on day 19 and on day 23 after the transplantation. Tumour volumes were measured twice a week and are shown as mean±SE of 15 mice per group. Arrows indicate anti PD-1 injections (*p<0.05; **p<0.01 Anova test).
Figure 4:
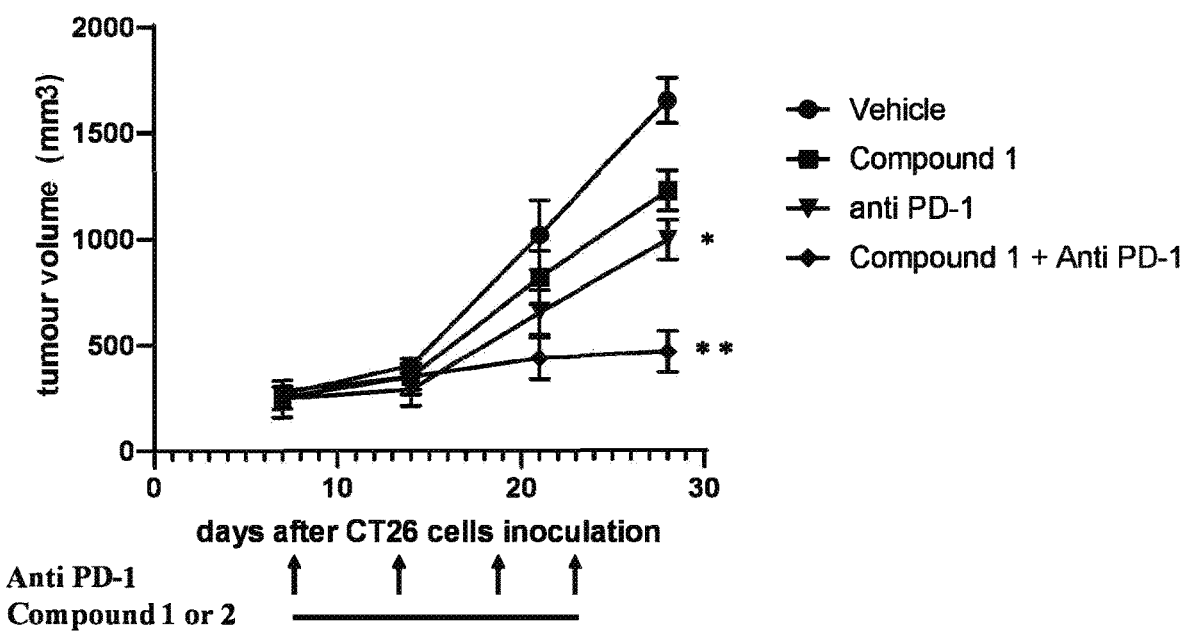
FIG. 4 reports the antitumor responses of Compound, anti-PD-1 and combined therapy in CT26 Tumor Models. Balb/c mice were subcutaneously injected with 1×10^6 CT26 cells. After tumors were measured on day 7, mice were randomized and then treated with the designated therapy. Compound 1 and Compound 2 were orally administered 30 mg/Kg daily. Anti PD-1 antibodies were injected 20 mg/kg on day 8 and 10 mg/kg on day 13, on day 19 and on day 22 after the transplantation. Tumour volumes were measured twice a week and are shown as mean±SE of 15 mice per group. Arrows indicate anti PD-1 injections (*p<0.05; **p<0.01 Anova test).

The graph of FIG. 3 reports the weekly measured tumour volumes plotted toward the days after tumoural cells inoculation. It can be seen that single therapy with Compound 1 had a mild inhibitory effect on cancer growth starting at the second week of treatment, whereas the compound of example 2 only showed a slight impairment of tumour growth. Anti mouse PD-1 therapy slowed cancer growth, even if, according to data reported in literature the inhibition of cancer growth was only partial. (Shindo, Y. et al. *Anticancer Res.* 35, 129-136 (2015)). On the contrary, as reported in FIG. 4 the anti tumour efficacy resulted significantly enhanced by the combination treatment with Compound 1 and anti mouse PD-1 antibody.

Figure 5:
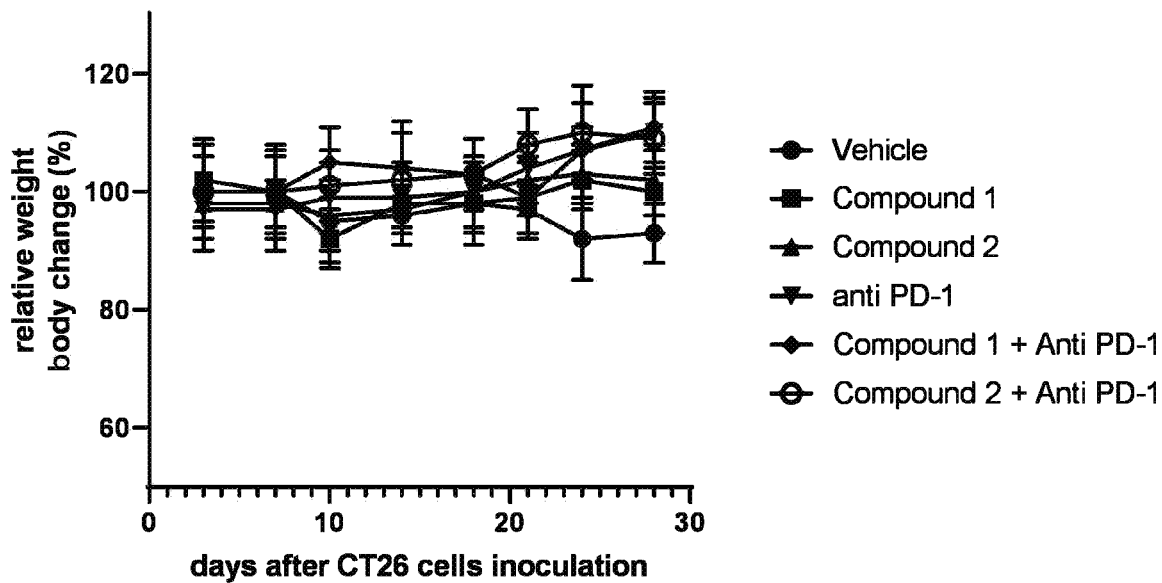
FIG. 5 reports the relative body weight change throughout treatment with Compound 1, the compound of example 2, anti PD-1 antibodies and combination therapy. Mice weight was measured twice weekly.

In addition, evaluation of animal body weight throughout the treatment showed that combination therapy did not affect general health of animals (FIG. 5).

Conclusions

The above reported results showed that Compound 1 and Compound 2 inhibit the tumour growth when given as single therapy. Furthermore, Compound 1 significantly enhances the anti-tumour effect of PD-1 antibody when used in combination.

EXAMPLE 4

Effect of Two EP4 Antagonists on 3H-PGE2 Specific Binding on Human Recombinant EP4 Receptor Subtypes Method Cell membranes were prepared from HEK293 cell line (Human Embryonic Kidney 293) stably overexpressing human recombinant EP4 receptor. Cells grow adherent in DMEM with Glutamax I containing 10% FBS at 37° C. with 5% $CO_2$. For membranes preparation, culture medium was aspirated from 150 $cm^2$ flasks in which cells were seeded. Cell monolayers were washed with 10 ml of hypotonic lysis buffer (TRIS 5 mM+EDTA 5 mM—pH 7.4), then cells were detached and lysed with the same buffer and by mechanical scraping. Lysates were centrifuged at 40000×g at 4° C. for 22 min. Pellets were stored at −80° C. until the use. [3H]-Prostaglandin E2 ([3H]-PGE2) binding assays were performed in 10 mM MES-KOH buffer pH6, containing 10 mM $MgCl2$ and 1 mM $CaCl2$. Ten microgram of protein from membrane fractions are incubated in a total volume of 0.1 ml with 1 nM [3H]-PGE2. In order to determine the total binding or the non specific binding, 1% DMSO or 1 μM PGE2 were added to reaction mixtures, respectively. The specific binding represented>85% of total binding. In competition curves, the diluent was substituted by the test compounds (8 concentration spanning at least 2 order of magnitude; points in duplicates). In an independent series of experiments, competition curves of the same compounds were performed in the presence of Bovine Serum Albumin 0.5%. Incubation was carried out in a 96 multiwell plate for 90 min at room temperature, prior to separation of the bound and free radioligand by rapid filtration on glass fiber filters (Unifilter GFB96, PerkinElmer Inc) pre-soaked in 0.3% polyethyleneimine. Filters were washed with ice cold buffer pH 7.4 (50 mM HEPES, NaCl 500 mM, BSA 0.1%), dried for 30 minutes at 30° C. and then 0.1 ml of MICROSCINT-20 (PerkinElmer Inc) were added. The residual [3H]-PGE2 binding was determined by solid scintillation counter (Top-Count, PerkinElmer Inc), after at least 1 hour of stabilization. Results of the competition curves were expressed as $IC_{50}$ and the corresponding Ki were calculated according to the Chang-Prousoff equation. Finally the Ki value was transformed in pKi (the negative log of Ki).

Results

Both the compounds under investigation showed nanomolar affinity to human recombinant EP4 receptor. However, in the presence of proteins (i.e. BSA), Compound 2 showed a 6-fold lower affinity, as stated by the lower value of pKi reported in the following table with respect to Compound 1 (7.5 and 6.7 in the absence or presence of BSA, respectively).

|  | pKi | |
| --- | --- | --- |
|  | None | BSA 0.5% |
| Compound 1 | 7.9 | 7.6 |
| Compound 2 | 7.5 | 6.7 |

Affinity of Compound 1 and Compound 2 (pKi) to human recombinant EP4 Receptor in absence or in presence of 0.5% BSA.

Conclusions

The results obtained suggest that the compound of example 2 has a higher binding potential to proteins (e.g BSA) in vitro if compared with Compound 1, thus influencing its interaction to the EP4R under study.

EXAMPLE 5

In Vitro Effect of Compound 1 on TNFα Release Induced by Lipopolysaccaride (LPS) and Modulated by Prostaglandin E2 (Rat Whole Blood Culture)

Material and Methods

Male Wistar Han rats (250-300 g b.w., Charles River, Italy) were housed six per cage in a temperature-controlled room, set to maintain temperature within the range of 20° C.±2° C. and relative humidity within the range of 55%±10 and with a 12-h/12-h light/dark cycle. Throughout the study animals had free access to standard laboratory chow (Teklad rodent diet 2018, Harlan Laboratories, S. Pietro al Natisone, UD, Italy) and drinking water. Care and handling of the animals were in accordance with the guidelines of the Local Government and the regulations of the European Community. Authorization for experimental procedures was granted by the Italian Ministry of Health. The day of the experiments animals were anaesthetized with 2.5-3% isoflurane in $O_2$ inside an induction chamber and blood was drawn from the abdominal aorta. Whole blood samples were collected in tubes containing 0.1-0.2 U/ml heparin. Aliquots (0.5 ml) were dispensed in a series of tubes and, after the addition of 0.1 µg/ml Lipopolysaccaride (E. coli serotype 055:65; LPS; Sigma Aldrich) (Control samples) or a mixture 0.1 µg/ml LPS+0.1 µM PGE2 (Cayman Chemical), samples were incubated at 37° C. in 5% CO2 incubator for 4 hours. The stimulant concentration selected was the lowest concentration from previous titration assays, that results in cellular activation; otherwise, it would be possible that modest alterations in cytokine production may be masked. Likewise, the time of stimulation was the optimal, short as possible, since the function of immune cells may potentially be affected once they are removed from the animal. After 4 hours of stimulation the cytokine release was almost maximal, being at plateau after 18-24 hours.

In samples representing basal release of the cytokine, LPS was substituted by the same volume of sterile PBS. LPS and PGE2 were prepared as a stock solution in sterile PBS+BSA 0.2%. At the end of incubation 10 mM EDTA was added and samples were centrifuged at 4° C. to obtain the plasma, which was subsequently stored in aliquots at −80° C. until ELISA assay for cytokine determination. The levels of TNF-α release in rat whole blood culture were evaluated using the Rat TNFalpha ELISA kit (Diaclone, France). Compared to the reference standard curve, TNF-α levels in samples were expressed as concentration (pg/ml).

Results

Figure 6:
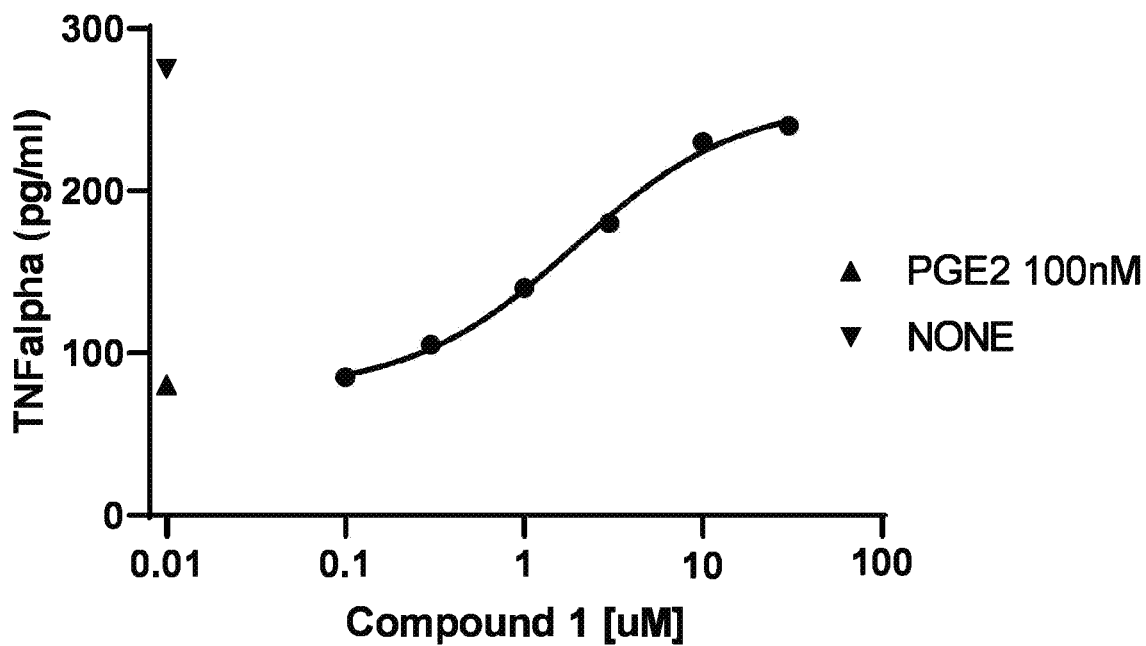
FIG. 6 reports in vitro concentration-dependent reversal of PGE2 effect by Compound 1.

The concentration-dependent reversal of PGE2 effect on TNF-α release by Compound 1 in vitro was demonstrated. A curve of Compound 1 (0.1-30 µM) towards a fixed PGE2 concentration determining about 80% of inhibition of TNF-α release allowed to calculate an $IC_{50}$ value 2.3 µM as shown in FIG. 6.

Conclusions

The inhibitory effect of PGE2 with respect to TNF-α production induced by LPS was useful to demonstrate in vitro the activity of the EP4 antagonist Compound 1. The results obtained in these experiments underline that Compound 1 reverts PGE2 reduction of TNF-α release in blood cells stimulated with LPS.

EXAMPLE 6

Ex Vivo TNF-α Release Induced by LPS: Linear Relationship between PGE2 Inhibition ($IC_{50}$) and Compound 1 Treatment Doses Material and Methods Male Wistar Han rats (250-300 g b.w., Charles River, Italy) were housed six per cage in a temperature controlled room, set to maintain temperature within the range of 20° C.±2° C. and relative humidity within the range of 55%±10 and with a 12-h/12-h light/dark cycle. Throughout the study animals had free access to standard laboratory chow (Teklad rodent diet 2018, Harlan Laboratories, S. Pietro al Natisone, UD, Italy) and drinking water. Care and handling of the animals were in accordance with the guidelines of the Local Government and the regulations of the European Community.

Authorization for experimental procedures was granted by the Italian Ministry of Health. Modulation of PGE2 (Cayman Chemical) effect on TNF-α release ex-vivo was assessed using whole blood culture samples from animals treated orally with vehicle or Compound 1 at different doses, and collected 1 hour after dosing.

In details the day of the experiments, animals were anaesthetized with 2.5-3% isoflurane in $O_2$ inside an induction chamber and blood (in average 7 ml/rat) was drawn from the abdominal aorta. Whole blood samples were collected in tubes containing 0.1-0.2 U/ml heparin. Aliquots (0.5 ml) were dispensed in a series of tubes, and after the addition of LPS (Control samples) or a mixture of 0.1 µg/ml LPS+different concentration of PGE2, samples were incubated at 37° C. in 5% $CO_2$ incubator 24 hours. In sample representing basal release of cytokine, LPS was substituted by the same volume of sterile PBS. LPS and PGE2 were prepared as 100× stock solution in sterile PBS+BSA 0.2%. At the end of incubation 10 mM EDTA was added, samples were centrifuged at 1500 g for 10 minutes at 4° C., plasma was removed and stored in aliquots at −80° C. until ELISA assay for cytokine determination. To analyze the levels of TNF-α release in rat whole blood culture the Rat TNFalpha ELISA kit (Diaclone, France) was used. Compared to the reference standard curve, TNF-α levels in samples were expressed as concentration (pg/ml).

For each animal, percent of inhibition by different PGE2 concentrations with respect to control sample, and the corresponding $IC_{50}$ (or the half-maximal inhibitory concentration in a range 0-100% inhibition) were calculated by linear regression analysis. Moreover, in each treatment group either the mean TNF-α levels and the mean % inhibition by PGE2 were calculated. Two-way ANOVA was performed in order to determine the statistically significant effect of each dose-treatment with respect to vehicle group and considering each point of PGE2 inhibition curve.

The mean $IC_{50}$ values for each group were plotted in function of Compound 1 dose administered, in order to calculate by linear regression analysis, the relationship between Compound 1 dose and resulting PGE2 $IC_{50}$.

Results

With the aim to demonstrate the modulatory activity of Compound 1 with respect to the known PGE2 inhibitory effect on TNF-α release, an ex-vivo model based on whole blood cultures stimulated with LPS was deployed. In particular, the ex-vivo effect of Compound 1 administered orally at five different doses, ranging from 10 mg/kg up to 300 mg/kg, was evaluated towards a PGE2 inhibition curve, in order to calculate a shift of the agonist $IC_{50}$ in the presence of the antagonist. TNF-α production induced by LPS 0.1 µg/ml was measured after 24 hours ex vivo stimulation. The blood sampling of 1 hour was chosen as representative of Compound 1 $t_{max}$ and the-low doses used (10-30 mg/kg) were according to its pharmacological activity, as measured previously in rat models of rheumatoid arthritis.

Figure 7:
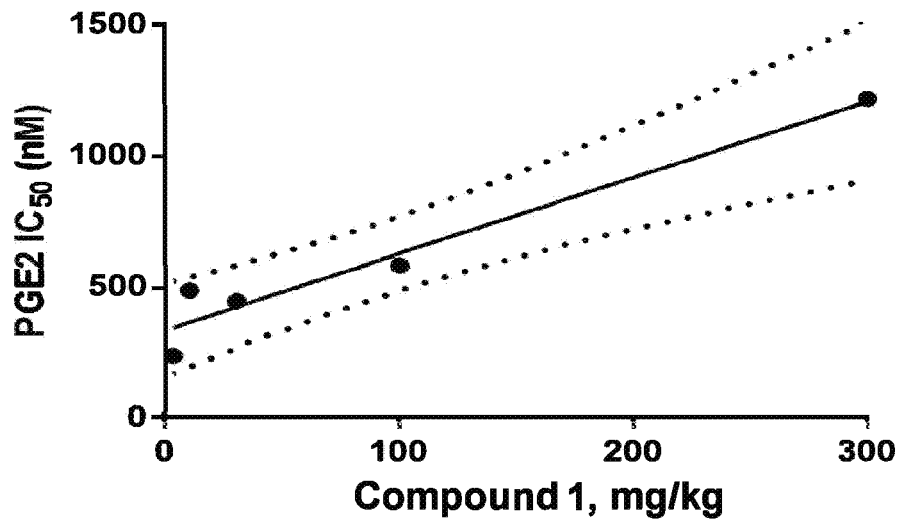
FIG. 7 reports the ex-vivo TNF-α release induced by LPS: linear relationship between PGE2 inhibition ($IC_{50}$) and Compound 1 treatment dose. Linear regression of analysis, R2=0.9268; P value for slope deviation to zero=0.0086.

PGE2 inhibited the cytokine release and the presence of Compound 1 in blood, interacting with EP4R, determined a statistically significant reversion of this effect. The PGE2 $IC_{50}$ value for the vehicle was calculated and an increase of this value by 3 up to 9-fold was observed as consequence of the treatment with Compound 1. The linear relationship between the dose of Compound 1 and PGE2 $IC_{50}$ value is represented in FIG. 7.

Figure 8:
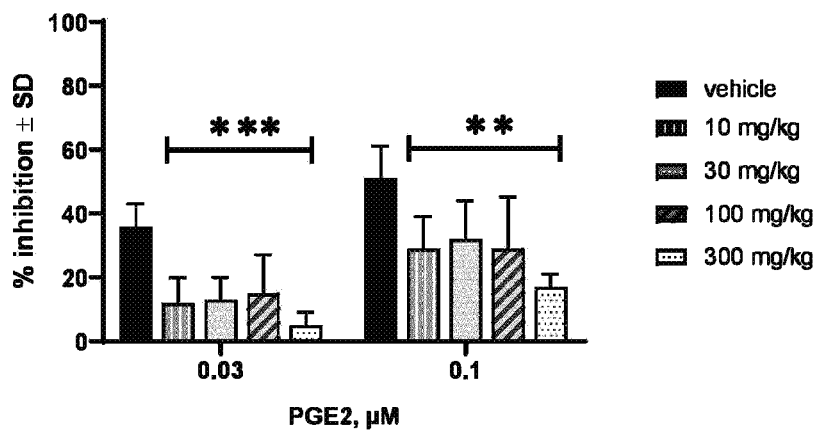
FIG. 8 reports the ex-vivo inhibition of TNF-α release in whole blood culture stimulated by LPS. Inhibitory effect of PGE2 0.03 µM and 0.1 µM after vehicle or Compound 1 administration in doses ranging from 10 mg/kg to 300 mg/kg. Two-way ANOVA analysis; p<0.001 vs vehicle; *p<0.0005 vs vehicle Dunnett's multiple comparisons test.

Consistent with the target engagement of Compound 1 to rat EP4R, the analysis of the ex-vivo release of TNF-α induced by LPS, inhibited by PGE2 and modulated by Compound 1 was focused with respect to low nanomolar concentration of PGE2, since these are representative of the range of concentrations that are usually observed in tumour microenvironment. Plotting the inhibitory effects on TNF-α release determined by PGE2 towards Compound 1 administered doses, a global dose-dependent reversion was observed for both PGE2 concentrations. Results are reported in FIG. 8.

Figure 9:
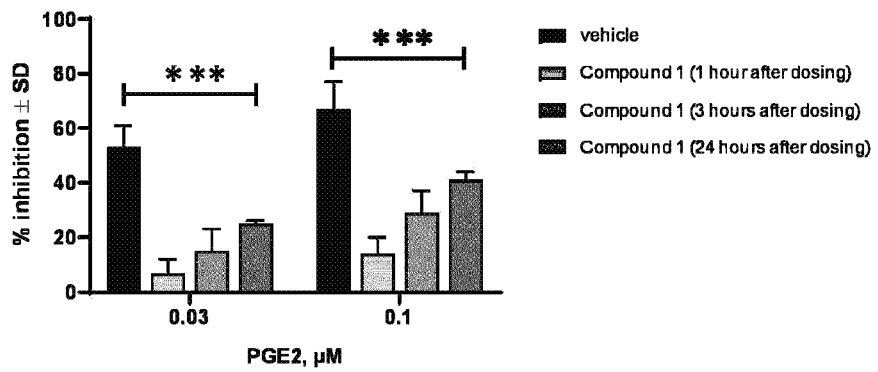
FIG. 9 reports the ex-vivo inhibition of TNF-α release in whole blood sampled at different time from dosing and ex vivo stimulated by LPS. Inhibitory effect of PGE2 0.03 µM and 0.1 µM after vehicle or 10 mg/kg Compound 1 administration. Two-way ANOVA analysis; ***p<0.0005 vs vehicle Dunnett's multiple comparisons test.

Furthermore a time course (1-3-24 hours) of blood sampling analysis highlighted the long lasting engagement of the EP4R by the minimum effective dose of 10 mg/kg Compound 1 since, as can be observed in the graph of FIG. 9, although a slight time dependent decrease of Compound 1 effect could be observed, the reversion of PGE2 TNF-α release inhibition was still evident also 24 hours after Compound 1 administration.

Conclusions

The inhibitory effect of PGE2 with respect to TNF-α production induced by LPS, was useful to demonstrate the activity of the EP4 antagonist Compound 1. Overall, these results strongly demonstrate the ability of Compound 1 to reverse the PGE2 induced inhibition of TNF-α release in blood cells. Indeed, in ex-vivo experiments, in which blood samples derived by animal treated orally with vehicle (control) or Compound 1 and collected 1 hour after dosing, the presence of the compound 1 determined a statistically significant reversion of the expected effect of PGE2. Moreover, the reversion of PGE2 TNF-α release inhibition was still evident also 24 hours after Compound 1 administration.

EXAMPLE 7

Ex-Vivo Effects of Compound 1 and Compound 2 Single Treatment on TNFα Release Induced by LPS and Inhibited by PGE2, 24 Hours After Dosing Modulation of PGE2 effect on TNF-α release ex-vivo was assessed using whole blood culture samples from Wistar Han rats (275-300 g b.w.) treated orally with vehicle, Compound 1 or the compound of example 2, both administered at 10 mg/kg. Blood samples were collected 24 hours after dosing.

Animals were housed six per cage in a temperature controlled room, set to maintain temperature within the range of 20° C.±2° C. and relative humidity within the range of 55%±10 and with a 12-h/12-h light/dark cycle. Throughout the study animals had free access to standard laboratory chow (Teklad rodent diet 2018, Harlan Laboratories, S. Pietro al Natisone, UD, Italy) and drinking water. Care and handling of the animals were in accordance with the guidelines of the Local Government and the regulations of the European Community. Authorization for experimental procedures was granted by the Italian Ministry of Health.

In details the day of the experiments, animals were anaesthetized with 2.5-3% isoflurane in O2 inside an induction chamber, and blood was drawn from the abdominal aorta. Samples were collected in tubes containing 0.1-0.2 U/ml heparin, aliquots (0.5 ml) were dispensed in a series of tubes, and after the addition of LPS 0.1 μg/ml (Control samples) or a mixture LPS+different concentrations of PGE2, they were incubated at 37° C. in 5% CO2 incubator for 4 hours. In samples representing basal release of cytokine, LPS was substituted by the same volume of sterile PBS. LPS and PGE2 were prepared as a stock solution in sterile PBS+BSA 0.2%. At the end of incubation 10 mM EDTA was added, samples were centrifuged at 1500 g for 10 minutes at 4° C., plasma was removed and stored in aliquots at −80° C. until ELISA assay for cytokine determination (Diaclone France).

Results

Figure 10:
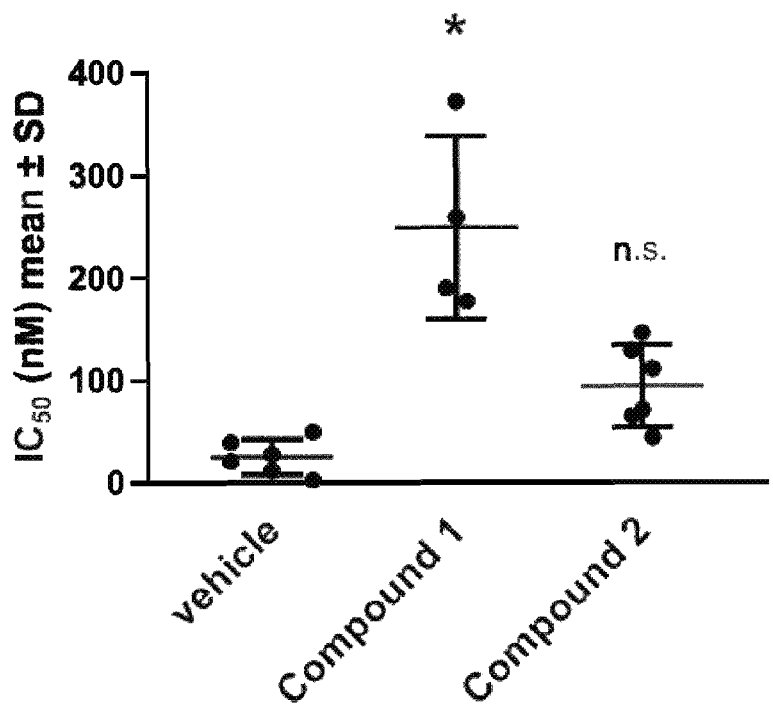
FIG. 10 reports PGE2 $IC_{50}$ values distribution: effect of Compound 1 (10 mg/kg) and Compound 2 (10 mg/kg) after single oral administration (24 hours after dosing). One way ANOVA *p<0.001 vs vehicle Dunnett's multiple comparisons test.

The PGE2 $IC_{50}$ values obtained in control (vehicle) or treated groups were analyzed. The presence of Compound 1 in blood, 24 hours after the administration, determined a statistically significant reversion of PGE2 inhibition of TNFα release induced by LPS, with respect to vehicle treated group (FIG. 10), in fact a 9-times statistically significant shift of the PGE2 $IC_{50}$ values was observed. On the contrary, in the presence of Compound 2, only a moderate, not statistically significant shift of the $IC_{50}$ values, with respect to vehicle treated group was observed. Both compounds did not interfere per se on the cytokine release.

Conclusions

The inhibitory effect of PGE2 with respect to TNF-α production induced by LPS was useful to demonstrate the activity of EP4 antagonists. Compound 1 was able to revert the PGE2 inhibitory effect on TNF-α release 24 hours after single oral dosing. On the contrary, the compound of example 2 only slightly reduced PGE2 inhibition without statistical significance.

EXAMPLE 8

Ex-Vivo Effect of Repeated Administration of Compound 1 on TNF-α Release Induced by Lipopolysaccharide and Modulated by Prostaglandin E2

Material and Methods

Male Wistar Han rats (250-300 g b.w.; Charles River, Italy) were housed six per cage in a temperature controlled room, set to maintain temperature within the range of 20° C.±2° C. and relative humidity within the range of 55%±10 and with a 12-h/12-h light/dark cycle. Throughout the study animals had free access to standard laboratory chow (Teklad rodent diet 2018, Harlan Laboratories, S. Pietro al Natisone, UD, Italy) and drinking water. Care and handling of the animals were in accordance with the guidelines of the Local Government and the regulations of the European Community. Authorization for experimental procedures was granted by the Italian Ministry of Health. Modulation of PGE2 effect on TNF-α release ex-vivo was assessed using whole blood culture samples from animals treated orally, qd for 8 days with vehicle or Compound 1 at 10 mg/kg, and collected 24 hours after the last treatment.

In details, the day of the experiments, animals were anaesthetized with 2.5-3% isoflurane in $O_2$ inside an induction chamber and blood was drawn from the abdominal aorta. Whole blood samples were collected in tubes containing 0.1-0.2 U/ml heparin. Aliquots (0.4 ml) were dispensed in a series of tubes pre-warmed at 37° C. for 10 minutes, and after the addition of LPS (Control) or a mixture LPS+different concentrations of PGE2, the samples were incubated at 37° C. in 5% CO2 incubator for 4 hours. In samples representing basal release of the cytokine, LPS was substituted by the same volume of sterile PBS. LPS and PGE2 were prepared as 100× stock solution in sterile PBS+BSA 0.2%. At the end of incubation 10 mM EDTA was added, samples were centrifuged at 1500 g for 10 minutes at 4° C., plasma was removed and stored in aliquots at −80° C. until ELISA assay for cytokine determination.

The levels of TNF-α release in rat whole blood culture were evaluated using the Rat TNFalpha ELISA kit (Diaclone, France).

Compared to the reference standard curve, TNF-α levels in samples were expressed as concentration (pg/ml). For each animal, percent of inhibition by different PGE2 concentrations with respect to control sample, and the corresponding $IC_{50}$ (or the half-maximal inhibitory concentration in a range 0-100% inhibition) were calculated by linear regression analysis. Moreover, in each treatment group either the mean TNF-α levels or the mean % inhibition by PGE2 were calculated. The PGE2 inhibition curve were graphically compared and the mean $IC_{50}$ values for each group were calculated.

Results

Figure 11:
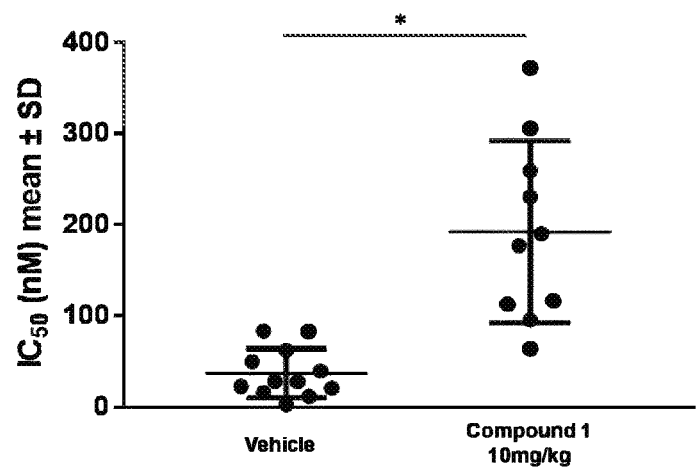
FIG. 11 reports PGE2 $IC_{50}$ values distribution: effect of Compound 1 10 mg/kg after repeated oral administration (qd for 8 days). *P<0.001 vs vehicle, Mann Withney test.

The effect of Compound 1 (10 mg/kg) administered orally qd for 8 days towards inhibition of PGE2 was evaluated 24 hours after the last treatment. The presence of Compound 1 in blood confirmed a statistically significant reversion of the inhibitory effect of PGE2, indeed the $IC_{50}$ values in control group treated with vehicle only are significantly lower than $IC_{50}$ values of 10 mg/kg Compound 1 treated group. In particular a 5-times and statistical significant increase of the mean $IC_{50}$ values in Compound 1 treated group with respect to the $IC_{50}$ values of controls was observed as shown in FIG. 11.

Conclusions

The results of the present study demonstrate that repeated dose-treatment of the compound 1 may modulate the PGE2 induced inhibition of TNF-α release in rat blood cells even 24 hours after the last dosing.

EXAMPLE 9

TNF-α Expression on In Vitro Culture of Human Macrophages

Material and Methods

The human monocyte cell line THP-1, obtained from the ATCC, was grown according to the instructions provided. THP-1 cells were differentiated to macrophages with 100 nM phorbol 12-myristate 13-acetate (PMA) (Sigma Aldrich) for 4 days. Macrophages were then stimulated with lipopolysaccharide (LPS) (Sigma Aldrich) 10 ng/ml and PGE2 0.01 μM for 3 hours. Total RNA was purified using the ABI Prism 6100 Nucleic Acid PrepStation (Applied Biosystems, Foster City, Calif., USA) and retrotranscribed using the High-Capacity cDNA Reverse Transcription Kit (Thermo Fisher Scientific). RT-PCR analysis was performed using the Applied Biosystems 7500 Fast Real-Time PCR System using specific TaqMan assays (number Hs00174128_m1; Thermo Fisher Scientific) and, as an endogenous control, the 18S Pre-Developed TaqMan® Assay (Thermo Fisher Scientific). The data analysis, with normalisation on 18S amplified values, was done following Thermo Fisher Scientific's specific instructions for gene expression relative quantification. All individual data are the result of at least three different analyses for each sample.

Results

To evaluate the Compound 1 potential in counteracting the PGE2 induced inhibition of TNF-α gene expression in human macrophages, THP-1 cells were differentiated to macrophages and subsequently treated with LPS 10 ng/ml plus PGE2 10 nM±Compound 1 in the 0.01 μM to 10 μM concentrations range for 3 hours.

Figure 12:
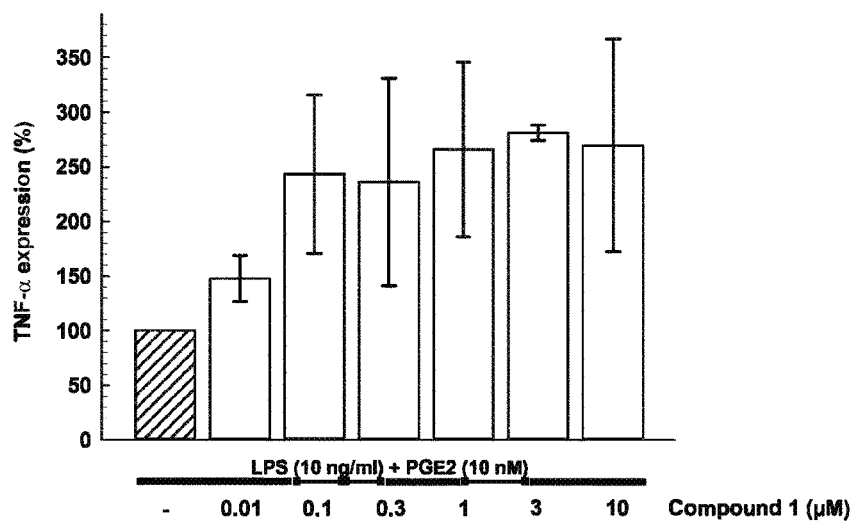
FIG. 12 reports that Compound 1 dose dependently reverses the PGE2 induced inhibition of TNF-α gene expression on human THP-1 cells differentiated to macrophages and stimulated with LPS 10 ng/ml plus 0.01 µM PGE2. Results are expressed as mean percentage of TNF-α expression±SD of independent experiments performed in triplicate. (LPS Lipopolysaccharide, PGE2 Prostaglandin E2).

As shown in the graph of FIG. 12, reporting the percentage of TNF-α gene expression in comparison to LPS+PGE2 stimulated human macrophages (set to 100%), Compound 1 increased TNF-α gene expression levels, achieving a two to three fold increase with respect to cells treated with PGE2+ LPS only at concentration as low as 0.1 μM.

Conclusions

These data provide evidence that Compound 1 modulates TNF-α expression levels and it counteracts the PGE2 induced inhibition of TNF-α expression in human immune cells such as macrophages.

EXAMPLE 10

Effect of Compound 1 on RANK-L Expression in Cancer Cell Lines

Material and Methods

The human mammary gland adenocarcinoma MDA-MB-231 cells were obtained from ATCC and grown according to the instructions provided.

Cells were treated with 10 μM PGE2±Compound 1 10 μM for 24 hours. Total RNA was purified using the ABI Prism 6100 Nucleic Acid PrepStation (Applied Biosystems, Foster City, Calif., USA) and retrotranscribed using the High-Capacity cDNA Reverse Transcription Kit (Thermo Fisher Scientific). RT-PCR analysis was performed using the Applied Biosystems 7500 Fast Real-Time PCR System using specific TaqMan assays (Hs00243522_m1; Thermo Fisher Scientific) and, as an endogenous control, the 18S Pre-Developed TaqMan® Assay (Thermo Fisher Scientific). The data analysis, with normalisation on 18S amplified values, was done following Thermo Fisher Scientific specific instructions for gene expression relative quantification. All individual data are the result of at least three different analyses for each sample.

Results

To evaluate whether Compound 1 could revert the increase of RANK-L gene expression induced by PGE2 on cancer cells, a model based on human breast cancer cells was employed.

MDA-MB-231 cells treated with 10 μM PGE2±Compound 1 10 μM for 24 hours and the levels of RANKL gene expression were evaluated by quantitative RT-PCR.

Figure 13:
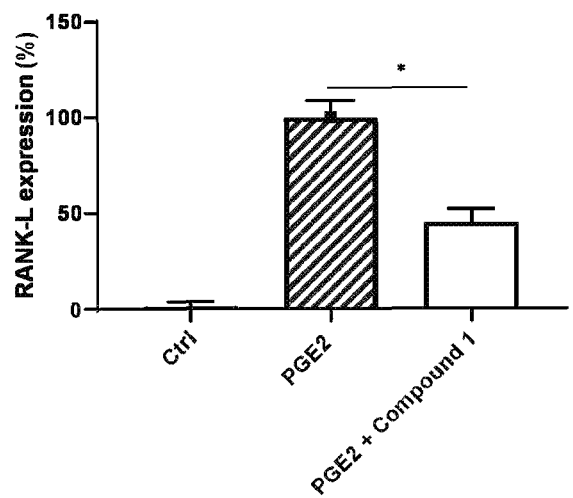
FIG. 13 reports that Compound 1 inhibited RANKL gene expression on human breast cancer cell line MDA-MB-231 stimulated with 10 µM PGE2. Results are expressed as mean percentage of RANK-L expression±SD of independent experiments performed in triplicate. *P<0.05 by one-way analysis of variance with Tukey-Kramer multiple comparisons test. PGE2 Prostaglandin E2.

Results are reported in the FIG. 13 where the mean percentage of RANK-L expression in comparison with cells stimulated with 10 μM PGE2 set to 100% are shown. Compound 1 markedly decreased the level of RANK-L gene expression.

Conclusions

Data obtained provide evidence that Compound 1, counteracting the PGE2 effect, reduces RANK-L gene expression in human cancer cells.

EXAMPLE 11

Ex Vivo Reduction of Human Th-17 Cells Differentiation

Material and Methods

Peripheral blood mononuclear cells (PBMC) were isolated from healthy volunteers using density gradient centrifugation and CD4+ naïve T cells were enriched from PBMCs using human naïve CD4+ T cell isolation kit (Miltenyi Biotech). Isolated CD4+ T cells were maintained in RPMI medium and differentiated toward Th-17 cells by stimulation with IL-12 and IL-2, both 5 ng/ml in combination with 1.5 ng/ml of antibodies anti CD3 and anti CD28 and 0.03 μM PGE2±Compound 1 at concentration of 0.01-0.03-0.1-0.3 μM for 48 hours.

At the end of incubation time cells were stained with fluorescence-conjugated antibodies specific for CD4, CCR6, CD45, CD25 and IL-17 (all from BD Bioscience). Finally, the number of Th-17 cells was determined by flow cytometry and the events were measured by Fluorescence Activated Cell Sorter (FACS; BD Bioscience) and analyzed with dedicated software.

Results

Figure 14:
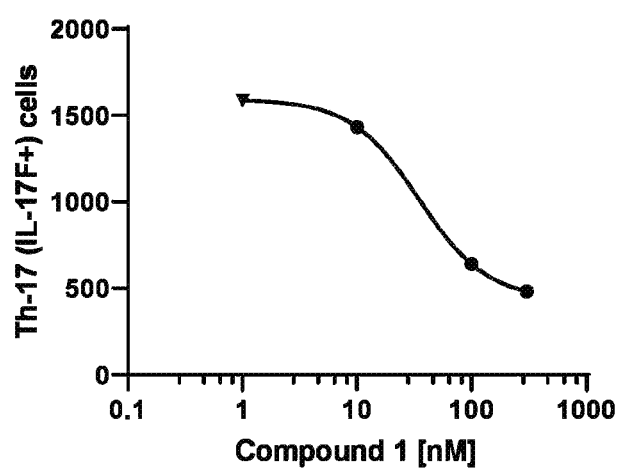
FIG. 14 reports that Compound 1 dose dependently decreased Th-17 frequency in human PBMC cells induced toward a Th-17 cells differentiation by exposure to IL-2, II-21, anti CD3 and CD28 antibodies and 0.03 µM PGE2. (Th-17 cells were gated as CD4+CCR6+CD45Ro-IL17F+).

The results obtained are reported in FIG. 14, where the frequency of Th-17 F+ cells are plotted toward Compound 1 concentrations. Compound 1 dose-dependently induced a marked decrease in the number of naïve Th-17 cells, reaching a plateau of maximal effect at concentrations above 0.1 µM.

Conclusion

Data obtained provide evidence that Compound 1 negatively modulates Th-17 cells differentiation.

EXAMPLE 12

Ex Vivo Human T Regulatory Cells Differentiation

Material and Methods

Peripheral blood mononuclear cells (PBMC) were isolated from healthy volunteers using density gradient centrifugation and CD4+ naïve T cells were enriched from PBMCs using human naïve CD4+ T cell isolation kit (Miltenyi Biotech). Isolated CD4+ T cells were maintained in RPMI medium and differentiated toward a Treg phenotype using two interleukins, namely, rIL23 and rIL-1β, both at a concentration of 10 ng/ml and co-stimulated with PGE2 at 30 nM concentration over a 144 hours incubation period.

At the end of incubation cells were stained with fluorescence conjugated antibodies specific for CD3, CD4, FoxP3, CD25, IL35 and CRTH2 (all from BD Bioscience). Finally, the number of Treg cells was determined by flow cytometry and the events were measured by Fluorescence Activated Cell Sorter (FACS; BD Bioscience) and analyzed with dedicated software.

Results

Figure 15:
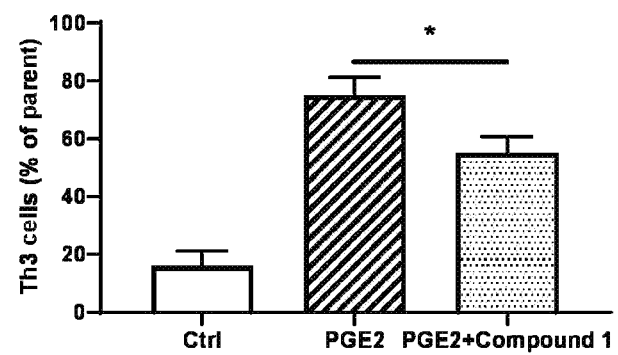
FIG. 15 reports that Compound 1 decreased Th-3 cells frequency in human PBMC cells induced toward Treg differentiation by exposure to rIL23 and rIL-1β (10 ng/ml) and treated with PGE2 0.03 µM±0.1 µM Compound 1. In the graph, the mean and standard deviation are reported. *p<0.05 One Way Anova. (Th-3 cells were gated as CD3+CD4+FoxP3+CD25low+TGFb+)
Figure 16:
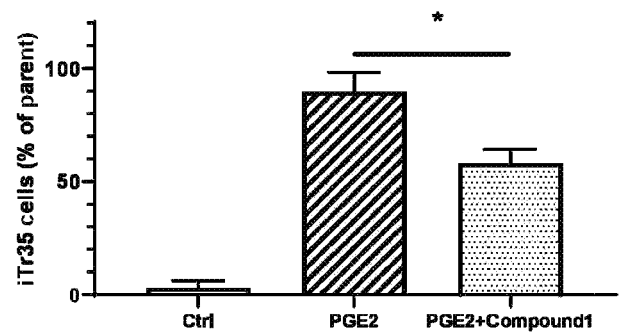
FIG. 16 reports that Compound 1 decreased iTr35 regulatory cells frequency in human PBMC cells induced toward Treg differentiation by exposure to rIL23 and rIL-1β (10 ng/ml) and treated with PGE2 0.03 µM±0.1 µM Compound 1. In the graph, the mean and standard deviation are reported. *p<0.05 One Way Anova. (iTr35 cells were gated as CD3+CD4+IL35+).

Regulatory T cells (Tregs), a subset of CD4+ T cells, have been found to play key roles in maintaining suppressive tumour microenvironment and thus contribute to cancer progression (Shindo, Y. et al. *Anticancer Res.* 35, 129-136 (2015)). PGE2 is a well known inducer of FoxP3 cells differentiation (Zhang, L. et al. *Cell Biol. Int.* 38, 639-646 (2014)). Data reported here underlined the efficacy of Compound 1 to decrease the ex vivo differentiation of Tregs induced by PGE2. Indeed, while 0.03 µM PGE2 significantly promoted the differentiation of FoxP3 positive cells, 0.1 µM Compound 1 significantly decreased Th-3 cells differentiation, as reported in FIG. 15. Th-3 cells are a particular subset of T regulatory cells whose activation and expansion in cancer is correlated to worst prognosis. (Durán-Aniotz, C. et al. *Cancer Immunol. Immunother.* 62, 761-772 (2013)). Furthermore, a similar inhibition of PGE2 induced differentiation was observed for another subpopulation of Treg cells, i.e. iTR35 cells, as reported in FIG. 16.

iTr35 cells are characterized by the production and release of the potent immune suppressive factor IL-35. In addition iTr35 cells are often found at high levels in breast and colorectal cancer, where they participate in tumour immunotolerance via suppression of effector T cells proliferation (Hao, S. et al. *Carcinogenesis* 39, 1488-1496 (2018); Ma, Y. et al. *Oncotarget* 7, 73003-73015 (2016)).

Conclusion

Data obtained provide evidence that Compound 1 negatively regulates T regulatory cells differentiation, therefore results shown strongly sustain the application of this compound in immune-oncology therapy aiming at restore immune response against cancer cells.

The invention claimed is:

1. A polymorphic form A of sodium salt of (R)-4-(1-(6-(4-(trifluoromethyl)benzyl)-6-azaspiro[2.5]octane-5-carboxamido)cyclopropyl)benzoic acid characterized by a powder XRD spectrum with peaks at values of the angle 2θ±0.2° of 4.3, 5.0, 5.8, 6.4, 7.1, 8.3, 8.7, 12.8, 15.3, 15.9.

2. A pharmaceutical combination comprising the polymorphic form A of the sodium salt of (R)-4-(1-(6-(4-(trifluoromethyl)benzyl)-6-azaspiro[2.5]octane-5-carboxamido)cyclo propyl)benzoic acid according to claim 1 and at least one immune checkpoint inhibitor.

3. The pharmaceutical combination according to claim 2, wherein the at least one immune checkpoint inhibitor is selected from the group consisting of PD-1 (Programmed Death-1), PD-L1 (Programmed Death-Ligand 1), CTLA-4 (Cytotoxic T lymphocyte Antigen — 4), TIM3 (T cell immunoglobulin and mucin-3), OX-40 and its ligand OX4OL, LAG-3 (lymphocyte activation gene-3), KIR (Killer-cell Immunoglobulin-like Receptor), VISTA (V-domain Ig-containing suppressor of T cell activation), IDO1 (Indoleamine 2,3-dioxygenase), TIGIT (T cell immunoglobulin and ITIM domain), BTLA (B and T lymphocyte attenuator), A2AR (Adenosine receptor A2), SIGLEC7 (Sialic acid-binding immunoglobulin-type lectin 7), GITR (Glucocorticoid-Induced TNFR family Related gene), ICOS (Inducible T-cell costimulator), NOX-2 (nicotinamide adenine dinucleotide phosphate NADPH oxidase isoform 2), Arginase I, CD276, CD27 (Cluster of Differentiation 27) and its ligand CD27 (Cluster of Differentiation 27), CD160 (Cluster of Differentiation 160) and CD39 (Cluster of Differentiation 39).

4. The pharmaceutical combination according to claim 3, wherein the at least one immune checkpoint inhibitor is selected from the group consisting of neutralizing antibodies anti PD-1, anti CTLA 4, anti TIM-3 antibodies or anti LAG-3 antibody.

5. A pharmaceutical composition comprising the polymorphic form A of the sodium salt of (R)-4-(1-(6-(4-(trifluoromethyl)benzyl)-6-azaspiro[2.5]octane-5-carboxamido)cyclopropyl) benzoic acid according to claim 1 and a pharmaceutically acceptable carrier.

6. A method for treatment of tumors comprising administering to a subject in need thereof the polymorphic form A of the sodium salt of (R)-4-(1-(6-(4-(trifluoromethyl)benzyl)-6-azaspiro[2.5]octane-5-carboxamido)cyclopropyl) benzoic acid according to claim 1.

7. A method for treatment of tumors comprising administering to a subject in need thereof the polymorphic form A of the sodium salt of (R)-4-(1-(6-(4-(trifluoromethyl)benzyl)-6-azaspiro[2.5]octane-5-carboxamido)cyclopropyl) benzoic acid according to claim 1 and at least one immune checkpoint inhibitor.

* * * * *